United States Patent
Hu et al.

(10) Patent No.: US 10,028,785 B2
(45) Date of Patent: Jul. 24, 2018

(54) APPARATUS AND METHOD FOR SELF-GUIDED ABLATION

(71) Applicant: Acublate, Inc., Los Altos, CA (US)

(72) Inventors: Bob Sueh-Chien Hu, Los Altos Hills, CA (US); Girish Ananth Narayan, Sunnyvale, CA (US); Byongho Park, San Jose, CA (US)

(73) Assignee: Acublate, Inc., Los Altos, CA (US)

( * ) Notice: Subject to any disclaimer, the term of this patent is extended or adjusted under 35 U.S.C. 154(b) by 516 days.

(21) Appl. No.: 14/616,312

(22) Filed: Feb. 6, 2015

(65) Prior Publication Data

US 2016/0008058 A1    Jan. 14, 2016

Related U.S. Application Data

(60) Provisional application No. 61/936,331, filed on Feb. 6, 2014.

(51) Int. Cl.
*A61B 18/18* (2006.01)
*A61B 18/14* (2006.01)
(Continued)

(52) U.S. Cl.
CPC .......... *A61B 18/1492* (2013.01); *A61B 18/02* (2013.01); *A61M 25/0147* (2013.01);
(Continued)

(58) Field of Classification Search
CPC ...... A61B 18/1492; A61B 2018/00642; A61B 18/02; A61B 2034/2048;
(Continued)

(56) References Cited

U.S. PATENT DOCUMENTS

| 5,441,499 A | 8/1995 | Fritzsch |
| 6,048,063 A | 4/2000 | Fritsch et al. |

(Continued)

FOREIGN PATENT DOCUMENTS

| WO | WO-03089997 A2 | 10/2003 |
| WO | WO-2015/120325 A1 | 8/2015 |

OTHER PUBLICATIONS

International search report and written opinion dated Jul. 8, 2015 for PCT Application No. US2015/014906.
(Continued)

*Primary Examiner* — Lindsey G Wehrheim
(74) *Attorney, Agent, or Firm* — Wilson Sonsini Goodrich and Rosati, P.C.

(57) ABSTRACT

An ablation catheter comprises an elongate catheter body and a branch electrode element. The elongate catheter body has a central axis, a distal end, and a proximal end. The elongate catheter body is configured to be steered within a heart chamber. The branch electrode element has a base end and a working end or tip. The base end is secured to the elongate catheter body at a location spaced proximally of the distal end and an effector on the working end. The branch electrode element is configured to evert when the distal end of the elongate catheter body is in a pulmonary vein ostium or os so that the effector can be selectively engaged against locations surrounding the pulmonary vein os which differ in radial direction and distance. One or more of linear or curved ablation patterns are generated on tissue adjacent the pulmonary vein os with the effector.

36 Claims, 16 Drawing Sheets

(51) Int. Cl.
*A61M 25/01* (2006.01)
*A61B 18/00* (2006.01)
*A61B 18/02* (2006.01)
*A61B 34/20* (2016.01)
*A61B 90/00* (2016.01)

(52) U.S. Cl.
CPC .............. *A61B 2018/0022* (2013.01); *A61B 2018/00202* (2013.01); *A61B 2018/00267* (2013.01); *A61B 2018/00375* (2013.01); *A61B 2018/00577* (2013.01); *A61B 2018/00642* (2013.01); *A61B 2018/00839* (2013.01); *A61B 2018/0212* (2013.01); *A61B 2018/1405* (2013.01); *A61B 2018/1432* (2013.01); *A61B 2018/1465* (2013.01); *A61B 2018/1475* (2013.01); *A61B 2034/2048* (2016.02); *A61B 2034/2051* (2016.02); *A61B 2090/065* (2016.02)

(58) Field of Classification Search
CPC ...... A61B 2034/2051; A61B 2090/065; A61B 2018/00202; A61B 2018/00267; A61B 2018/00375; A61B 2018/00577; A61B 2018/00839; A61B 2018/0212; A61B 2018/1405; A61B 2018/1432; A61B 2018/1465; A61B 2018/1475; A61M 25/0147
See application file for complete search history.

(56) References Cited

U.S. PATENT DOCUMENTS

| | | |
|---|---|---|
| 6,272,371 B1 | 8/2001 | Shlomo |
| 6,402,746 B1* | 6/2002 | Whayne ............ A61B 18/1492 128/898 |
| 7,008,418 B2 | 3/2006 | Hall et al. |
| 7,097,643 B2 | 8/2006 | Cornelius et al. |
| 8,636,731 B2 | 1/2014 | Falwell et al. |
| 8,657,815 B2 | 2/2014 | Mody et al. |
| 2004/0215186 A1* | 10/2004 | Cornelius .......... A61B 18/1492 606/41 |
| 2005/0187545 A1 | 8/2005 | Hooven et al. |
| 2007/0270686 A1 | 11/2007 | Ritter et al. |
| 2009/0312755 A1 | 12/2009 | Thapliyal et al. |
| 2010/0049099 A1 | 2/2010 | Thapliyal et al. |
| 2010/0168620 A1 | 7/2010 | Klimovitch et al. |
| 2010/0191232 A1 | 7/2010 | Boveda |
| 2010/0274239 A1 | 10/2010 | Paul et al. |
| 2011/0184406 A1 | 7/2011 | Selkee |
| 2011/0213364 A1 | 9/2011 | Davis et al. |
| 2012/0165815 A1 | 6/2012 | Collins et al. |
| 2012/0184953 A1 | 7/2012 | Spence et al. |
| 2013/0116688 A1 | 5/2013 | Kunis et al. |
| 2016/0199127 A1* | 7/2016 | Prutchi ............. A61B 18/1492 606/41 |

OTHER PUBLICATIONS

Zhao; et al., Pulmonary antrum radial-linear ablation for paroxysmal atrial fibrillation: interim analysis of a multicenter trial. Circ Arrhythm Electrophysiol. Apr. 2013;6(2):310-7. doi: 10.1161/CIRCEP.113.000196. Epub Feb. 22, 2013.
European search report and search opinion dated Aug. 17, 2017 for EP Application No. 15746061.9.

* cited by examiner

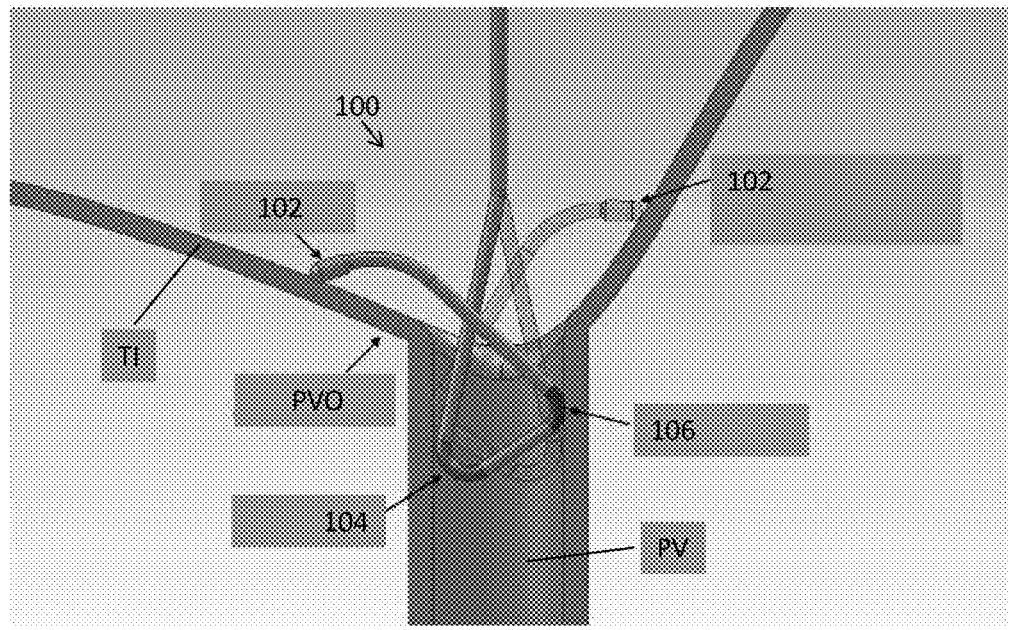
Fig. 1
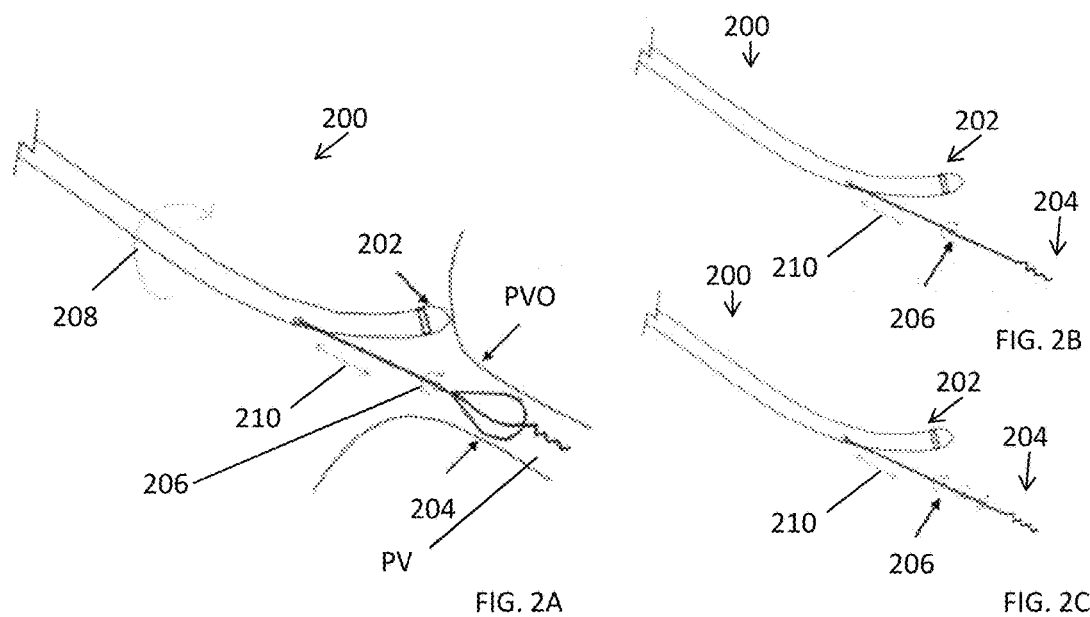
FIG. 2A
FIG. 2B
FIG. 2C

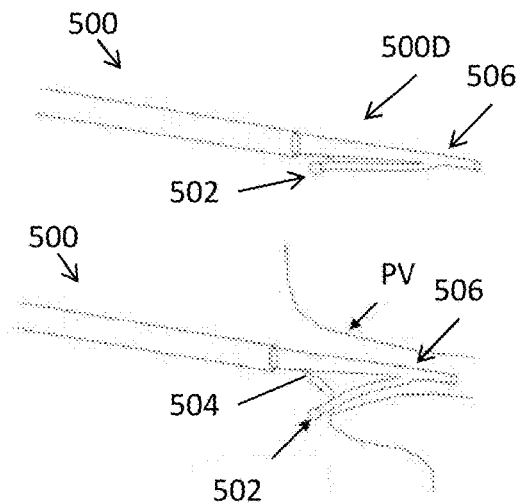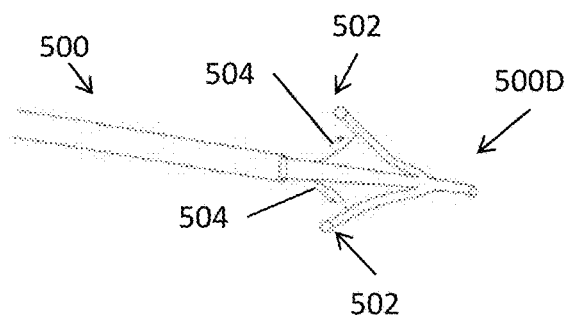
FIG. 5A     FIG. 5B
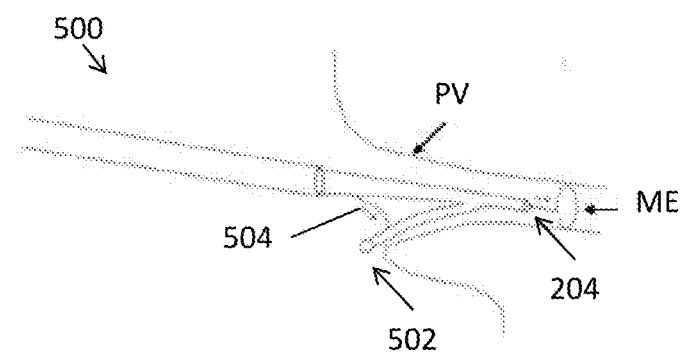
Fig. 6
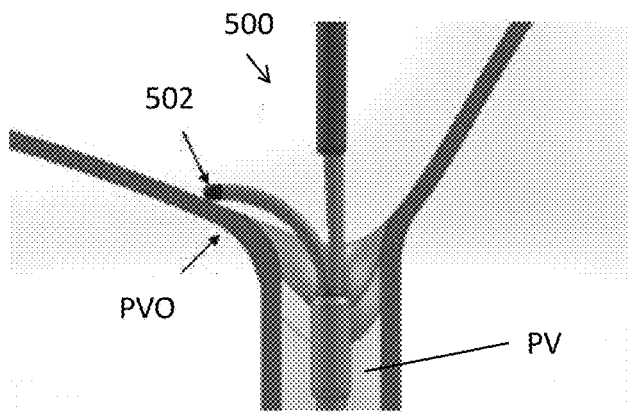
Fig. 7

APPARATUS AND METHOD FOR SELF-GUIDED ABLATION

CROSS-REFERENCE

This application claims the benefit of U.S. Provisional Application No. 61/936,331, filed Feb. 6, 2014, which application is incorporated herein by reference.

BACKGROUND

The present disclosure relates to medical systems, devices, and methods, particularly for the treatment of atrial fibrillation (AF). AF is by far the most common arrhythmic heart disorder in the United States. AF may affects some 2 million people and can account for some 500,000 hospital admissions a year. AF can increase the risk of stroke by some 5-fold and can lead to almost 80,000 deaths annually. While most patients with AF can be managed adequately with conservative medical therapy, a large number of patients can develop complications to the medicines used to treat the disease including fatigue, lightheadedness, or substantial bleeding. Furthermore, a substantial number of patients may be unable to tolerate AF due to disabling symptoms. Drugs that are used to prevent AF may not be very effective and can have potentially serious long term complications. While open surgical approaches like the Cox-Maze procedure may be shown to be quite effective in treating the disorder, less invasive catheter-based techniques may be successful only about 60% of the time. Given the enormous number of these procedures, even a modest improvement in therapeutic outcomes can have a large public-health impact.

Catheter ablation has had enormous success in the treatment of many heart rhythm disturbances. A well-placed destruction of the conductive property of cardiac tissue may interrupt the abnormal conduction pathway which may be the basis for essentially all heart arrhythmia. While catheter ablation may be highly successful in the treatment of conditions where the offending conduction disturbance is well known and localized, such as accessory conduction pathways or atrial flutter, its success in treating the most common arrhythmia of AF has been modest. The procedure can require several hours of anesthesia, radiation, and the use of multiple catheters with their attendant risks even in the hands of skilled operators. There are therefore needs for an ablation catheter that simplifies the mechanics of the creation of the contiguous electrical-isolation lines in the ablation procedure. Such an improved ablation catheter may increase the success rate of the procedure for patients while greatly reducing the associated cost of these procedures. There are also needs for self-navigating catheter apparatuses and systems that can provide a robust ablation system to greatly simplify the invasive treatment of atrial fibrillation.

AF is one of the most common cardiovascular disorders in the developed world. AF can be prevalent (e.g., about 10% of the population over the age of 70 may be afflicted), can cause up to $1/3$ of all strokes, and may respond only modestly to medications. While much of the risk of AF's most feared consequence, stroke, can be reduced with long-term blood-thinner treatments, substantial morbidity and mortality may still exist. Because of the potential complications for long term anticoagulation and because a substantial degree of morbidity in patients may be symptomatic, the ablation of atrial fibrillation is one of the most practiced intracardiac procedures. However, current percutaneous therapy for AF may not have the success rate sufficient to be attempted in most AF patients. Even in carefully selected patients, the success rate may only be 60-70%. Recently the direct visualization of atrial "rotors" has been developed. While many are cautiously hopeful, the impact of such development on the success of AF ablation may remain unknown. In contrast, the surgical treatment of atrial fibrillation using the modified Cox-Maze procedure is successful in greater than 90% of patients. The surgical success suggests that the shortcomings of percutaneous approaches to AF ablation may be due to solvable technical hurdles.

The greater space and freedom of intracardiac interventions may complicate both ablation target identification and device control, which may make the procedures complex, time-consuming, and less successful. There are therefore needs for ablation catheter apparatuses which are self-navigating such that a complete pulmonary vein isolation procedure can be performed in less than one hour.

The standard ablation AF target may be based on anatomic isolation of the pulmonary veins. Promising recent data generated in relation to embodiments of the present disclosure suggest that a physiologic approach of identifying "rotors" sources in AF may also be important. The ablation of identified AF ablation targets may be suboptimal due to the difficulty of accurate catheter placement for contiguous ablations and monitoring treatment.

The following references may be of interest: U.S. Patent Application Publication Nos. 2007/0270686, 2009/0312755, 2010/0049099, 2010/0168620, 2010/0191232, 2011/0184406, 2012/0184953, and 2013/0116688; and U.S. Pat. Nos. 6,272,371, 7,008,418, 7,097,643, 8,048,063, and 8,657,815.

SUMMARY

The present disclosure relates to medical systems, devices, and methods, particularly for the treatment of atrial fibrillation. Embodiments of the present disclosure provide ablation catheter apparatuses based on self-navigated, "foolproof" methods of proscribed ablation lines. The ablation catheter apparatuses may be steerable but ultimately self-navigated and may be used to produce reliable RF ablation that may be constrained to produce contiguous ablation patterns. The ablating tips of such catheter apparatuses may be variably deflectable so that the catheter apparatuses may be used to produce both linear and circular ablation lesions. In some embodiments, the catheter tips may even be deflectable in a reverse direction. In some embodiments, the catheter tips may include force feedback sensors. In some embodiments, rotation sensors may be embedded in the distal tips of the catheter apparatuses. Such self-navigated ablation catheters may significantly improve the accuracy of the rapidly expanding procedure of cardiac ablation for AF while reducing the procedure time. Such ablation catheter apparatuses, systems, and methods may drastically alter the treatment options available for one of the most common heart problems that affect one in four persons in their lifetime.

Ablation catheter apparatuses according to embodiments of the present disclosure can also be manufactured inexpensively. Unlike other catheters that may trade-off essential features to conform to the variable geometry of the pulmonary antrum, the ablation catheter apparatuses herein may include the full features, including irrigation and point-by-point pressure application, with few if any trade-offs.

Aspects of the present disclosure provide methods of ablating tissue. An elongate or elongated body of an ablation catheter may be advanced or directed into a body cavity. For example, the elongate body may be advanced through a cardiac chamber, through a pulmonary vein ostium, and into the lumen of a pulmonary vein. The distal end of the elongate body may be placed a tributary, branch, or outpouching to the cavity, for example, a venous structure, an arterial structure, or an appendix. By placing the distal end of the elongate body therein, mechanical stabilization or guidance of the ablation catheter inside the anatomical structure, for example, the pulmonary vein, may be provided. Guidance of the ablation catheter may be carried out by aligning the longitudinal axis of the ablation catheter relatively parallel to the longitudinal axis of the pulmonary vein. An ablation or interventional tip or effector attached to the elongate body may be deployed. The distal end of the ablation tip may be initially oriented toward the proximal end of the elongate body and then laterally deflected away from the elongate body toward the distal end of the elongate body when deployed. The deployed ablation tip may be oriented away from the elongate body of the ablation catheter. The ablation tip may be moved in a prescribed manner as constrained by the position of the distal end of the elongate body. For example, the ablation catheter may comprise a distal anchor which is seated within the pulmonary vein lumen and which the ablation tip may be rotated about or translated relative to in a limited range. The ablation tip may be moved predominately in a rotational, linear, or mixed rotational and/or linear manner around the tributary, branch, or outpouching. For example, the ablation tip may be moved by linearly translating the ablation tip via pushing the distal tip in and out of the tributary, branch, or outpouching. The distal or other anchor may comprise a suture, a clip, or an expandable element such as a balloon or a wire cage. The ablation tip may be delivered to interact with tissue such as by ablating or otherwise modifying the characteristics of the tissue, for example, the cardiac tissue adjacent the pulmonary vein ostium. The ablation may be configured for one or more of the delivery of RF energy, thermal heating, or cooling for cryoablation.

Aspects of the present disclosure also provide medical devices for modifying tissue. A medical device may comprise an ablation or interventional tip and means for stabilizing the medical device inside a pulmonary vein. For example, the means for stabilizing the medical device may comprise sutures, clips, anchors, inflatable balloons, wire cages, or the like as further described herein. The medical device may comprise means for determining the orientation of the interventional tip. For example, the means for determining orientation may comprise an accelerometer, a gyroscope, a magnetometer, an optical position indicator, a magnetic position indicator, or the like as described herein. The means for determining orientation may further comprise an external system with external sensors that detect and map the position of the ablation tip in three-dimensional space. The means for determining orientation of the ablation tip may be connected to an external unit for displaying and bookmarking. The means for determining orientation of the ablation tip may provide localization information with combination and current use of external beacons or reference. The medical device may further comprise means for irrigation. The medical device may further comprise means for detecting contact force between the ablation tip and tissue, such as a binary switch with a prescribed force value. The ablation tip may have a pre-shaped curvature relatively close to the curvature of the pulmonary vein. The means for stabilizing inside the pulmonary vein may have a free-rotation joint that allows the ablation tip to rotate freely. The means for stabilizing inside the pulmonary vein may not be anchored to the pulmonary vein. The distal end of the ablation tip may be able to determine the profile of the pulmonary vein or map electrical signals.

Aspects of the present disclosure provide further medical devices for modifying tissue. A medical device may comprise an elongate or elongate body and a rotational sensor embedded therein. The rotational sensor may comprise a 6-axis accelerometer and gyroscope. The rotational sensor may be combined with externally applied fields to provide three dimensional localization of the elongate body.

Aspects of the present disclosure also provide ablation catheters comprising an elongate catheter body and a branch electrode element. The elongate catheter body may have a central axis, a distal end, and a proximal end. The elongate catheter body may be configured to be steered within a heart chamber. The branch electrode element may have a base end and a working end or tip. The base end may be secured to the elongate catheter body at a location spaced proximally of the distal end and an effector on the working end. The branch electrode element may be configured to evert when the distal end of the elongate catheter body is in a pulmonary vein ostium or os so that the effector can be selectively engaged against locations surrounding the pulmonary vein os which differ in radial direction and distance.

The branch electrode element may be curved when everted. The curvature of the branch electrode element may match a curvature of a pulmonary vein or the pulmonary vein os.

The ablation catheter may further comprise a constraint coupled to the branch electrode element to adjust an amount of eversion of the branch electrode element. The constraint may be configured to be translated relative to one or more of the elongate catheter body or the branch electrode element to adjust the amount of eversion of the branch electrode element. The constraint may be annular and may circumscribe one or more of the elongate catheter body or the branch electrode element. The ablation catheter may further comprise a push-pull wire coupled to the elongate catheter body and the constraint. The push-pull wire may be configured to be translated to adjust the amount of eversion of the branch electrode element. The push-pull wire may be configured to be proximally retracted to reduce the amount of eversion of the branch electrode element.

The ablation catheter may further comprise a core wire disposed within the elongate catheter body. The core wire may have a coaxial distal portion disposed within the elongate catheter body and a lateral arm coupled to the straight coaxial distal portion and disposed within the branch electrode element. Proximal retraction of the core wire may cause the lateral arm to extend laterally outward, everting the branch electrode element. Distal advancement of the core wire may straighten the lateral arm, reducing eversion of the branch electrode element.

The ablation catheter may further comprise a distal anchor extending from the distal end of the elongate catheter body. The distal anchor may be configured to be seated within a lumen of the pulmonary vein. The distal anchor may be coaxial with the central axis of the elongate catheter body. The branch electrode element may be rotatable with respect to the distal anchor. The distal anchor may comprise one or more mapping electrodes.

The effector may comprise an ablation electrode. The branch electrode element may comprise a sensor to detect one or more of contact force or pressure with tissue, an orientation of effector, or a position of the effector. The sensor may comprise one or more of an accelerometer, a strain gauge, an optical indicator, a magnetic position indicator, or a piezoelectric element. The branch electrode element may comprise a deflectable or compliant section, which may comprise one or more rotational joints and annular segments.

Aspects of the present disclosure also provide methods for pulmonary vein ablation. A distal end of a catheter may be anchored in a pulmonary vein os or ostium. A branch electrode element which carries an ablation element may be deployed to a plurality of locations surrounding the pulmonary vein. The branch electrode element may be deployed by independently controlling the radial direction and radial distance of the ablation element from the catheter.

To anchor the distal end of the catheter in the pulmonary vein os, an expandable element may be expanded in the pulmonary vein. The expandable element may comprise a wire cage or an inflatable balloon. The expandable element and one or more of the branch electrode element or catheter may be independently rotatable.

In many embodiments, tissue surrounding the pulmonary vein os may be mapped with one or more mapping electrodes disposed on the distal end of the catheter.

In many embodiments, an ablation pattern on tissue adjacent the pulmonary vein os may be generated with the ablation element. The ablation pattern may be generated by rotating the catheter to generate a curved ablation pattern with the ablation element. Alternatively or in combination, the ablation pattern may be generated by axially translating the catheter to generate a linear ablation pattern with the ablation element. Alternatively or in combination, the ablation pattern may be generated by adjusting an amount of eversion of the branch electrode element relative to the catheter. Alternatively or in combination, the ablation pattern may be generated by delivering energy from the ablation element to the tissue. The energy delivered may comprise one or more of RF energy or thermal energy. The ablation element may comprise an ablation electrode. Alternatively or in combination, the ablation pattern may be generated by delivering a cooling fluid for cryoablation.

In many embodiments, a tissue contact force between the ablation element and tissue surrounding the pulmonary os may be determined such as with a sensor adjacent the ablation element. In many embodiments, one or more of an orientation or position of the ablation element may be determined such as with a sensor adjacent the ablation element.

Aspects of the present disclosure may also provide ablation catheters comprising an elongate catheter body and a branch electrode element. The elongate catheter body may have a central axis, a distal end, and a proximal end. The elongate catheter body may be configured to be steered within a body cavity. The body cavity may be selected from the group comprising a nasal cavity, an oral cavity, a throat, an esophagus, a stomach, a small intestine, a large intestine, a colon, a rectum, a bronchus, a bladder, a ureter, a urethra, a vagina, a cervix, a uterus, a fallopian tube, a heart chamber, a heart ventricle, a heart atrium, an aorta, a vena cava, an abdominal aorta, a renal artery, a femoral artery, an ascending aorta, a subclavian artery, a carotid artery, a jugular vein, a subclavian vein, a cephalic vein, a femoral vein, a renal vein, an inferior vena cava, or a pulmonary artery, to name a few. The branch electrode element may have a base end and a working end. The base end may be secured to the elongate catheter body at a location spaced proximally of the distal end and an effector on the working end. The branch electrode element may be configured to evert when the distal end of the elongate catheter body is in the body cavity so that the effector can be selectively engaged against tissue locations surrounding an opening into the body cavity which differ in radial direction and distance. The ablation catheter may further comprise any of the features of the ablation catheters described above and herein.

Aspects of the present disclosure may also provide methods for tissue ablation. A distal end of a catheter may be anchored in an opening into a body cavity. The body cavity may be selected from the group comprising a nasal cavity, an oral cavity, a throat, an esophagus, a stomach, a small intestine, a large intestine, a colon, a rectum, a bronchus, a bladder, a ureter, a urethra, a vagina, a cervix, a uterus, a fallopian tube, a heart chamber, a heart ventricle, a heart atrium, an aorta, a vena cava, an abdominal aorta, a renal artery, a femoral artery, an ascending aorta, a subclavian artery, a carotid artery, a jugular vein, a subclavian vein, a cephalic vein, a femoral vein, a renal vein, an inferior vena cava, or a pulmonary artery, to name a few. A branch electrode element which carries an ablation element may be delivered to a plurality of tissue locations surrounding the opening into the body cavity. The branch electrode element may be deployed by independently controlling the radial direction and radial distance of the ablation element from the catheter. The method may further comprise any of the steps and/or features of the ablation methods described above and herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 1 is a side view of a pre-shaped ablation catheter apparatus having primary and secondary bends and placed in an asymmetrically shaped pulmonary vein ostium, according to many embodiments;

FIG. 2A is a side view of a catheter apparatus with a laterally facing ablation tip and a free-rotation joint in parallel to both the longitudinal axis of a pulmonary vein and the longitudinal axis of the catheter apparatus, according to many embodiments;

FIG. 2B is a side view of a catheter apparatus with a laterally facing ablation tip and a free-rotation joint parallel to the longitudinal axis of the catheter apparatus, according to many embodiments;

FIG. 2C is a side view of a catheter apparatus with a laterally facing ablation tip and multiple free-rotation joints parallel to the longitudinal axis of the catheter apparatus, according to many embodiments;

FIG. 5A is a side view of a catheter apparatus with a single ablation tip that can be expanded and deployed relatively perpendicular to longitudinal axis of a pulmonary vein, according to many embodiments;

FIG. 5B is a side view of a catheter apparatus with double ablation tips that can be expanded and deployed relatively perpendicular to longitudinal axis of a pulmonary vein, according to many embodiments;

FIG. 6 is a side view of a catheter apparatus with an expandable ablation tip and a centering mechanism deployed at its distal end, according to many embodiments;

FIG. 7 is a side view of the catheter apparatus of FIG. 6 naturally placed around the pulmonary vein ostium by reversely deploying away from the funnel, according to many embodiments;

DETAILED DESCRIPTION OF THE INVENTION

Figure 3:
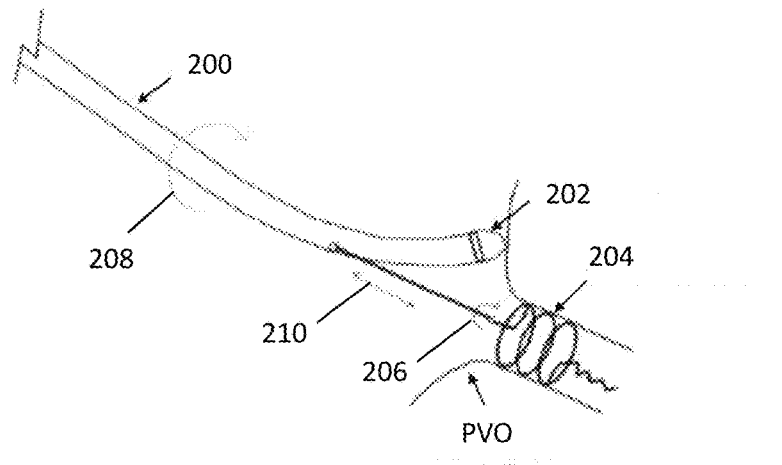
FIG. 3 is a side view of a catheter apparatus with an anchoring mechanism that has a free-rotation point placed in the pulmonary vein ostium, according to many embodiments.

Embodiments of the present disclosure provide steerable and self-guided ablation catheters. Ablation catheter apparatuses of the present disclosure may provide a fault-tolerant, self-centered, pre-shaped catheter apparatus with fine local control of the catheter tip to deliver a desired ablation pattern in the left atrium. The ablation catheter may be integrated with and operated by an intuitive control system. FIG. 1 shows a pre-shaped ablation catheter 100 with an effector or ablation tip 102 that can be constrained to a locus of contiguous points that circumscribes the antrum of the pulmonary vein PV. The ablation catheter 100 may comprise a primary bend 104 distal of the main elongate body of the ablation catheter 100 and a secondary bend 106 proximal of the ablation tip 102 and distal of the primary bend 104. By taking advantage of the shape and limited diameter of the pulmonary vein PV, the catheter apparatus 100 may be constrained to prescribe a contiguous locus of ablation points even with a variable contour. FIG. 1 illustrates the self-centering and contiguous target seeking characteristics of the ablation catheter apparatus 100. It can be important to ensure adequate reach and a good contact force between the ablation tip 102 and the tissue TI to create reliable ablation lesions, particularly so that ablation does not lead to charring with minimal contact or damage heart tissue with excessive contact. Considering many anatomical variations based on patient imaging datasets, the shape of the distal ablation tip 102 may be optimized to accommodate a range of antrum geometries in terms of the distal tip contact angle and orientation. For example, a set of design parameters for the catheter apparatus 100 may include one or more of (i) the angle in the primary bend 104, (ii) the angle in the secondary bend 106, (iii) the angle in the ablation tip 102, (iv) the curvature length in the primary bend 104, (v) the curvature length in the secondary bend 106, (vi) the distance between the primary bend 104 and the secondary bend 106, and (vii) the distance between the secondary bend 106 and the ablation tip 102. The angle of the primary bend 104 may be between 5 degrees and 175 degrees, preferably between 40 degrees and 160 degrees. The angle of the secondary bend 106 may be between 10 degrees and 150 degrees, preferably between 30 degrees and 120 degrees. The tip 102 may also be bent with a bend angle of between 0 degrees and 90 degrees, preferably between 10 degrees and 50 degrees. The segment length may be between 5 mm and 50 mm, preferably between 5 mm and 30 mm. The diameter of the segments may be between 1 mm and 5 mm, preferably between 2 mm and 4 mm.

The ablation catheter 100 can fit and work in a wide range of pulmonary vein PV sizes. The pulmonary vein PV size can extend from 10 mm up to 20 mm in diameter. It can be imperative to ensure a good contact force against the tissue TI. The contact force can be determined by the stiffness of compliant segments in the catheter tip 102, i.e. primary bend 104, the secondary bend 106, and the ablation tip joint. Additional design parameter such as stiffness may therefore be considered in the construction of the ablation catheter 100, including stiffness in the primary bend 104, stiffness in the secondary bend 106, and stiffness in the ablation tip 102. The compliant segments can be made of metals (e.g. Stainless Steel, Ni—Ti alloy (Nitinol), Cobalt-Chrome alloy, Platinum, etc.). The stiffness of the compliant segments may be measured in rotational stiffness (newton-meters per radian). The rotational stiffness may be between 0.0001 and 1 (N-m/rad), preferably between 0.0005 and 0.2 (N-m/rad).

In order to deploy the ablation catheter 100 inside the pulmonary vein PV, the catheter tip 102 may be delivered through a guide sheath with a limited inner diameter. The catheter tip 102 may be constructed such that it can be delivered through the guide sheath safely and deployed once it is placed within the left atrium. Such delivery may require the catheter tip 102 to change its shape from almost a linear or straight line to a circular loop, which may induce a large strain and stress in the catheter tip 102. In order to meet the requirement, the tip 102 may comprise a material that can endure a large strain along the length. Materials such as stainless steel or other alloys may have limited working range, so such materials may reach yield stress under less than 1% strain. However, superelastic alloys such as Nitinol (nickel titanium alloy) may have ideal material properties to meet the mechanical requirements undergoing a large strain (3% or higher). Also, it can be important to provide enough mechanical support to ensure a good contact between the ablation tip 102 and tissue TI. In order to provide the optimal support, the Nitinol can be designed and processed in a form of tubular mechanical structure for the ablation catheter apparatus 100. A micromachining process may be used to change the mechanical stiffness of superelastic alloys at various points within the same tubular structure. As an example, the tubular body of the catheter apparatus 100 and other catheter apparatuses of the present disclosure described herein may be constructed to match the desired material characteristics with a layer of Nitinol or other superelastic alloy on the order of a 100 μm scale. Such a construction may leave the manufacturable size of the catheter substantially unaltered and may leave the existing capability of flushing and force application untouched. The pre-shaped catheter 100 can be constructed to limit its ablation locus to a contiguous but mostly fixed distance around the pulmonary antrum. Limited adjustment of that distance may be helpful to place the ablation lesion either closer or further from the pulmonary vein ostium PVO. The distance adjustment can be incorporated with a local actuator at the distal tip 102. The pre-shaped ablation catheter 102 can be positioned into several shapes that could be selected by the operator prior to the procedure. By pushing the ablation catheter 100 in and out of the pulmonary vein PV, the fixed distance of the ablation location relative to the pulmonary vein PV can be adjusted in a radial direction. So, the ablation tip 102 can create a linear lesion around the pulmonary vein PV by starting proximally and moving distally away from the pulmonary vein PV, or vice versa.

Referring to FIGS. 2A, 2B, and 2C, an ablation catheter apparatus 200 may comprise a deflectable effector or ablation tip 202 branching or extending laterally outward from the main body of the ablation catheter apparatus 200 and a deployable centering device or mechanism 204 at the distal end of the catheter apparatus 200 to locate and secure the ablation tip 202 relatively around the center of a pulmonary vein ostium PVO. The deployable centering mechanism 204 may be biased to be coaxial with the main body of the ablation catheter apparatus 200. The deployable centering mechanism 204 may be disposed in a lumen of the main body of the ablation catheter apparatus 200 and translatable therethrough. The distal end of the centering mechanism 204 can be placed inside a pulmonary vein PV or further beyond. The centering mechanism 204 may have a free-rotation point 206 (shown by FIGS. 2A and 2B) or multiple free-rotation points 206 (shown by FIG. 2C) to allow the ablation tip 202 to rotate freely around the axis of the centering mechanism 204. The distal end of the centering mechanism 204 may not be physically or permanently fixed to the proximal end of the mechanism 204, so the proximal side of the centering mechanism 204 can freely rotate while the distal end of the centering mechanism 204 may be securely placed inside or beyond a pulmonary vein PV. As shown in FIG. 2A, the free-rotation point 206 can allow the ablation tip 202 to freely rotate around the longitudinal axis of the centering mechanism 204 which is relatively parallel to the axis of the pulmonary vein PV. The free-rotation point 206 can be located just axially distal the distal ablation tip 202. As shown in FIG. 2C, a series of free-rotation points 206 can be placed or implemented to provide more flexibility and smooth rotation around a pulmonary vein PV. In some embodiments, the centering mechanism 204 can be used as a mapping device with an electrode or multiple electrodes embedded around the outer surface in contact with a pulmonary vein PV. The ablation catheter apparatus 200 can be rotated about the longitudinal axis of the proximal portion of the centering mechanism 204 and/or the longitudinal axis of the ablation catheter apparatus 200 along the arrow 208, for example, to generate a contiguous ablation lesion about the pulmonary vein ostium PVO. The rotation may be clockwise and/or counter-clockwise. Alternatively or in combination, the ablation catheter apparatus 200 may be axially translated along the direction indicated by double-sided arrow 210 to position the centering mechanism in the pulmonary vein PV and/or to generate a linear ablation lesion extending outwardly from the pulmonary vein ostium PVO.

Referring to FIG. 3, the centering mechanism 204 can be directly anchored inside a pulmonary vein PV. Once anchored, the distal tip, end, or portion 204D of the centering mechanism 204 may be stationary relative to the pulmonary vein PV, but the proximal tip, end, or portion 204P of the centering mechanism 204 may, from the free-rotation point 206, be free to rotate around the longitudinal axis of the centering mechanism 204. Such rotation can ensure that the ablation tip 202 which may be secured to the proximal portion 204P of the centering mechanism 204 can be able to smoothly rotate without any whipping issue or inconsistent rotational motion.

Figure 4A:
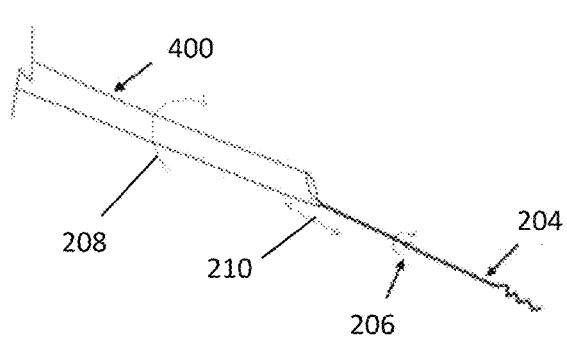
FIG. 4A is a side view of a guide sheath with a centering mechanism, according to many embodiments.
Figure 4B:
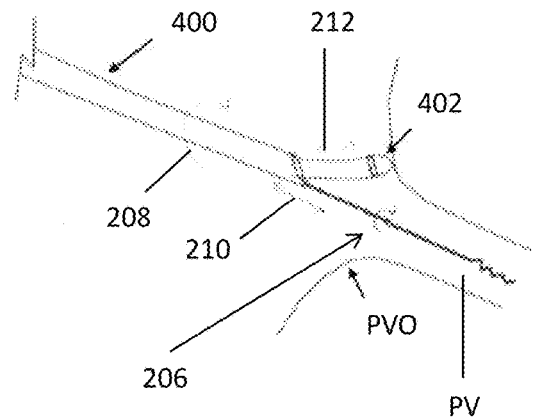
FIG. 4B is a side view of an ablation tip of an ablation catheter apparatus extending from the guide sheath of FIG. 4A, according to many embodiments.

Referring to FIGS. 4A and 4B, the centering mechanism 204 can be incorporated into a guide sheath 400. Many variations of ablation catheters can be used together or be compatible with the guide sheath 400 with the centering mechanism 204. The guide sheath 400 incorporating the centering mechanism 204 may be used to allow smooth rotation of an ablation tip 402 of an ablation catheter as indicated by arrow 208 in FIG. 4B. The centering mechanism 204 can be integrated as a part of the guide sheath 400 or may not be permanently fixed to the guide sheath 400. The guide sheath 400 with the centering mechanism 204 incorporated may be compatible with many existing ablation catheters that are commercially available from various companies. In some embodiments, the centering mechanism 204 can have a circular shape at its distal tip or end with mapping electrodes, similar to a Lasso mapping catheter. These electrodes can be used to map the electrical activities of the pulmonary vein PV in real-time during ablation while the centering mechanism 204 is placed inside the pulmonary vein PV.

Referring to FIGS. 5A and 5B, a centering mechanism 506 can be integrated as a part of the ablation tip 502. As shown in FIG. 5, the distal end 500D of the ablation catheter apparatus 500 can be expandable and extend out sideway when engaged or activated in a direction indicated by arrow 504. There can be two legs in the distal or working end 500D of the ablation catheter apparatus 500. At least one of the legs with an effector or ablation electrode 502 may extend proximally and laterally outward from the longitudinal axis of the ablation catheter apparatus 500 when deployed. The other leg may remain coaxial or parallel with the longitudinal axis of the main body of the ablation catheter apparatus 500. This leg may be integral with and continuous from the main elongate body of the ablation catheter apparatus 500. At least one of the legs, such as the laterally and proximally branching or extending leg, may have the ablation electrode 502, so the electrode 502 can comes in contact with the tissue TI just outside of the pulmonary vein PV when expanded out relatively perpendicular to the longitudinal axis of the ablation catheter apparatus 500. The leg or branch with the ablation electrode 502 may also be referred to herein as a branch electrode element. The two legs can allow the ablation catheter apparatus 500 to be securely positioned around the pulmonary vein ostium PVO. Alternatively or in combination, the previously described centering mechanism 204 can be deployed or delivered through the center of the ablation catheter apparatus 500 at the distal end to provide more secure positioning and smooth rotation of the ablation tip or electrode 502 while moving from one ablation point to the next one. In some embodiments, the distal end 500D of the ablation catheter apparatus 500 may have three legs with one leg coaxial or parallel with the main body of the catheter apparatus 500 and the others each branching or extending laterally outward and proximally and having ablation tips or electrodes 502 as shown in FIG. 5B (i.e., the ablation catheter apparatus 500 may comprise two branch electrode elements).

FIG. 6 illustrates how a centering device or mechanism 204 with a circular shape at its distal end or tip can be delivered through the ablation catheter apparatus 500. The centering mechanism 204 may also work as a mapping device with an electrode or multiple electrodes ME embedded around the outer surface in contact with a pulmonary vein PV.

Referring to FIG. 7, the ablation tip 502 can be deployed or be oriented in a reverse direction, so the distal segment of the ablation tip 502 is pointing toward the proximal end of the ablation catheter apparatus 500, or away from the pulmonary vein PV. Once deployed, the overall orientation or shape of the ablation tip 502 can match well with the natural funnel shape of the pulmonary vein PV. FIG. 7 illustrates a typical funnel shape of the pulmonary vein PV with the ablation tip 502 placed inside the pulmonary vein PV. The similarity of the anatomical geometry with that of the deployed ablation tip 502 can provide significant advantages in ensuring good contact around the ostium PVO at various orientations while rotating around the longitudinal axis of the pulmonary vein PV.

Figure 8:
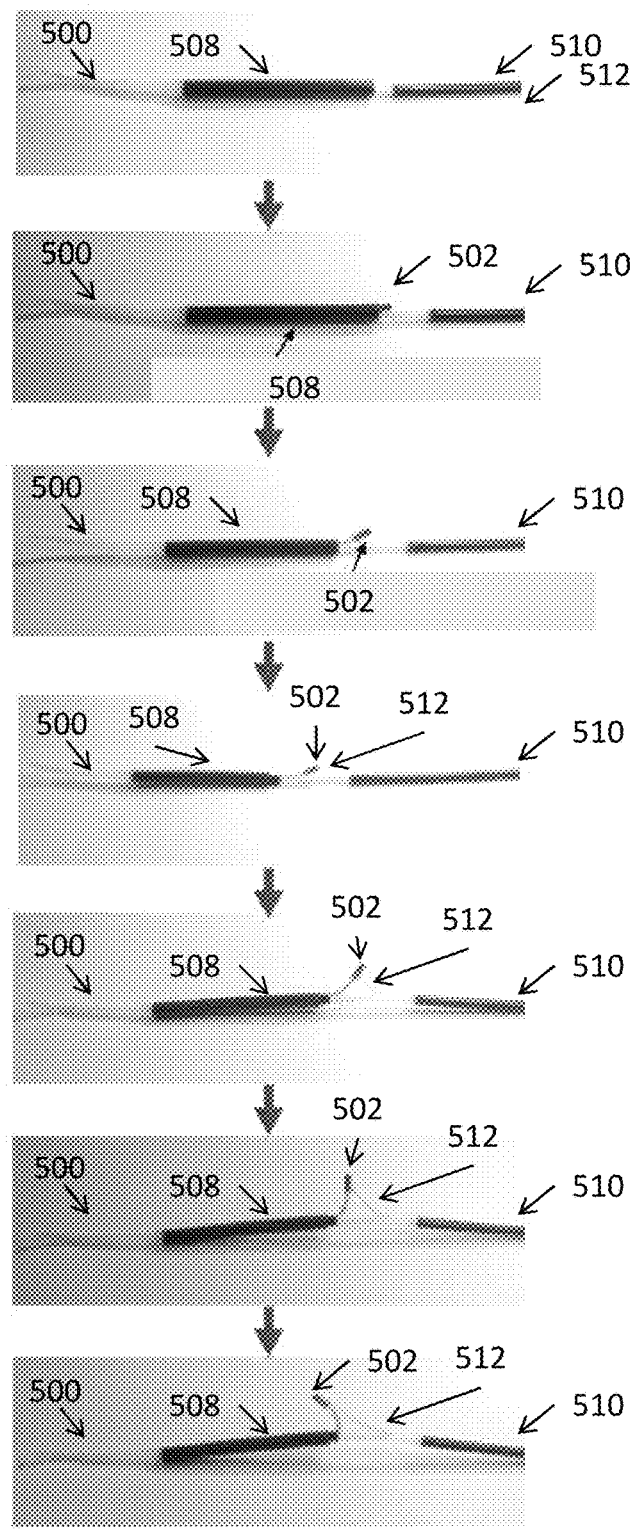
FIG. 8 is a side view of the deployment of the ablation tip of a catheter apparatus as the distal sheath slides out, according to many embodiments.

The deployment of the ablation tip 502 can be done through unsheathing at the distal end of the catheter apparatus 500 once delivered to a target area. The catheter apparatus 500 may comprise a ring, sheath, or constraint 508 which may be proximally retracted. As shown in FIG. 8, the ablation tip 502 can be deployed to a predetermined shape as the distal sheath 508 is retracted and moved away from the ablation tip 502. For example, the ablation tip 502 can be pre-shaped by a shape memory material such as Nitinol. As the distal sheath 508 is moved further away proximally, the radial distance of the ablation tip 502 from the longitudinal axis of the catheter apparatus 500 can increase such that the ablation tip 502 can reach further out. By adjusting or controlling how much the sheath 508 is moved, the degree of contact the ablation tip 502 has with the surrounding tissue TI or pulmonary vein PV can be controlled. Alternatively or in combination, the ablation catheter apparatus 500 may comprise a wire 512 coupled the body 510 of the ablation catheter apparatus 500 and to the ablation tip 502. As described further below and herein, the wire 512 may be advanced distally to push the ablation tip 502 further proximally and laterally. The adjustability and control thereby provided by the sheath or constraint 508 and/or the wire 512 can allow the catheter apparatus to accommodate different sizes and shapes of the pulmonary vein PV in variable anatomies of the hearts.

Figures 9A, 9B:
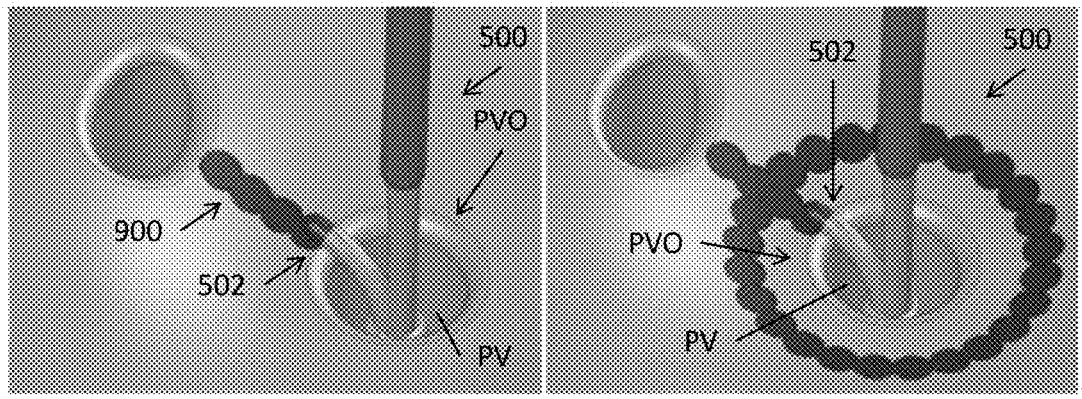
FIG. 9A is a perspective view of the generation of a linear ablation lesion with an ablation catheter apparatus, according to many embodiments.
FIG. 9B is a perspective view of the generation of a circular ablation lesion created by the ablation catheter apparatus, according to many embodiments.

FIGS. 9A and 9B show how the ablation catheter apparatus 500 can create a circular lesion 910 as well as a linear lesion 900 around the pulmonary vein PV. By rotating the ablation tip 502, the ablation catheter apparatus 500 can create a contiguous circular pattern 910 as shown by FIG. 9B. Also by pulling and pushing in the ablation tip 502 or sliding the distal sheath 508 in and out, the ablation catheter apparatus 500 can create a linear lesion 900 at a fixed orientation or angle without further rotational movement. A circular lesion 910 around a pulmonary vein ostium or os PVO may be generated for Pulmonary Vein Isolation (PVI) therapy. One or more linear lesions 900 adjacent a pulmonary vein ostium or os PVO may be generated for Pulmonary antrum radial-linear ablation (PAR) as described, for example, by X. Zhao et al., "Pulmonary Antrum Radial-Linear Ablation for Paroxysmal Atrial Fibrillation: Interim Analysis of a Multicenter Trial," *Circ Arrhythm Electrophysiol.* 2013; 6:310-317 (Feb. 22, 2013). While ablation or other tissue modification of tissue around a pulmonary vein ostium or os PVO is described, the ablation catheter apparatuses 100, 500, and others described herein may be used for tissue modification or ablation in other anatomical locations. For example, the ablation catheter apparatuses described herein may be precisely navigated in the renal artery for precision renal denervation to treat hypertension. The application of the ablation catheter apparatuses described herein is also contemplated for other body cavities, including but not limited to the nasal cavity, oral cavity, throat, esophagus, stomach, small intestine, large intestine, colon, rectum, bronchus, bladder, ureter, urethra, vagina, cervix, uterus, fallopian tube, heart chamber, heart ventricle, heart atrium, aorta, vena cava, abdominal aorta, renal artery, femoral artery, ascending aorta, subclavian arteries, carotid artery, jugular vein, subclavian vein, cephalic vein, femoral vein, renal vein, inferior vena cava, pulmonary artery, other blood vessels, and other body cavities.

Figures 10A, 10B:
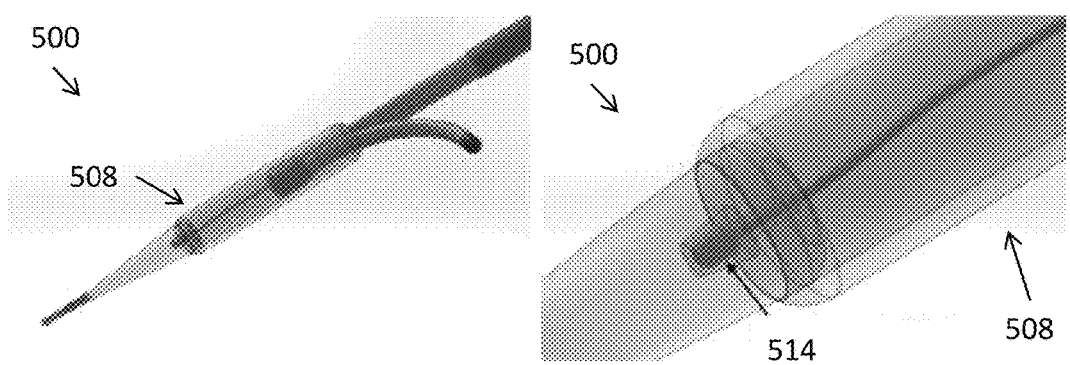
FIG. 10A is a perspective view of a distal sheath of a catheter apparatus with a free-rotation joint that allows free rotation of its ablation tip, according to many embodiments.
FIG. 10B is a magnified view of the free-rotation joint of the catheter apparatus of FIG. 10A.

In some embodiments, the distal sheath 508 can have a joint that is not permanently attached to the rest of the catheter apparatus 500 to allow the ablation tip 502 to freely rotate around or inside the distal sheath 508. FIGS. 10A and 10B show an example of the free rotation joint 514 in the distal sheath 508.

The ablation tip 502 can be further activated or deflected through an interface in the proximal handle such as a simple pull, push or rotation motion by a user. The activation or deflection of the tip 502 can ensure that enough contact force is applied between the ablation tip 502 and the tissue to create a good ablation lesion. Also, the deflection can be used to further change the overall shape of the ablation tip 502 and how far the ablation tip 502 moves away from the pulmonary vein ostium PVO. The activation mechanism can be implemented through a simple pull or push wire inside the ablation tip 502 as described further below and herein.

Figures 11A, 11B:
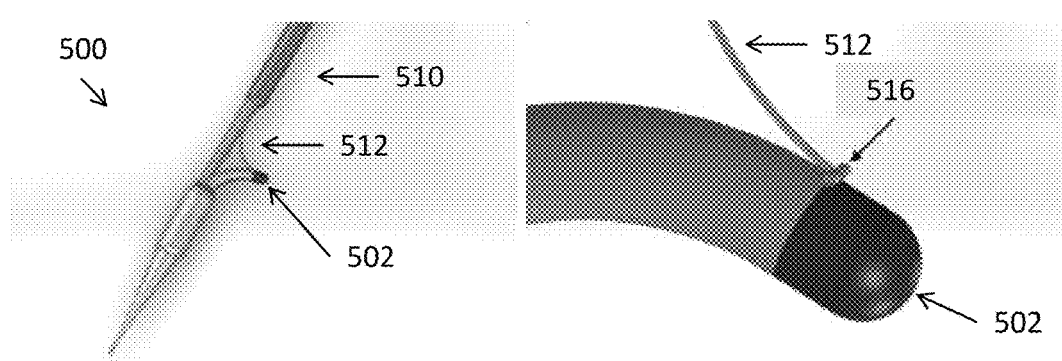
FIG. 11A is a side view of a catheter apparatus with an external wire/cable and hinge mechanism for activation or deflection of its ablation tip, according to many embodiments.
FIG. 11B is a magnified view of the hinge mechanism of the catheter apparatus of FIG. 11A.
Figure 12:
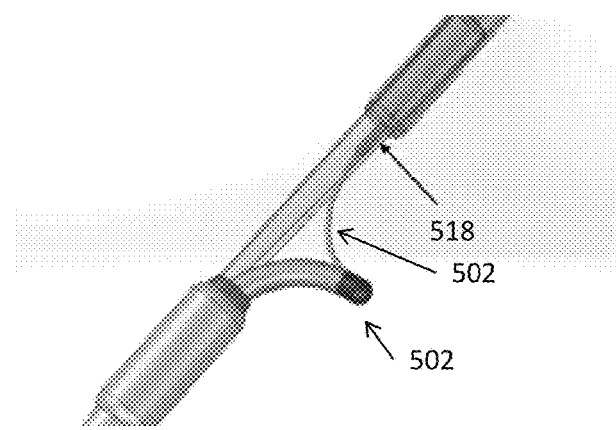
FIG. 12 is a magnified view of a simple contact and force sensing mechanism embedded along the push/pull wire of a catheter apparatus, according to many embodiments.
Figure 13A:
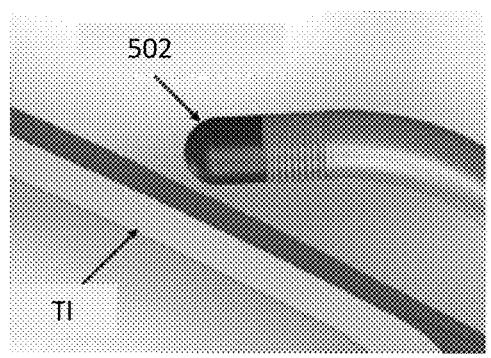
FIG. 13A is a perspective view of an ablation tip with a compliant structure for contact/force sensing on the distal tip of a catheter apparatus, according to many embodiments.
Figure 13B:
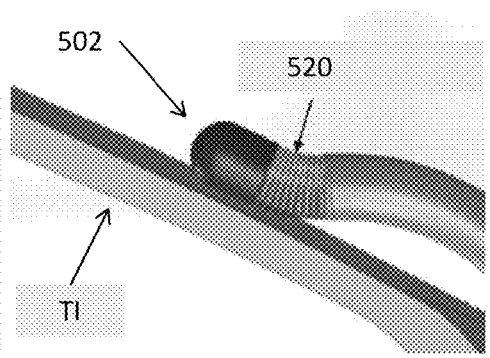
FIG. 13B is a perspective view of an ablation tip with a compliant structure for contact/force sensing on the distal tip of a catheter apparatus, according to many embodiments.

Alternatively or in combination, a pull or push wire 512 can be placed or attached to the ablation tip 502 externally through a small hinge mechanism 516 as shown in FIGS. 11A and 11B. The external wire or cable 512 can provide relatively direct translation of the movement from the proximal end of the ablation catheter 500, so it can provide more consistent and reliable activation or deflection at the distal ablation tip. FIG. 11B illustrates an example of the hinge mechanism 516 at the ablation tip 502. The hinge mechanism 516 can allow the ablation tip 502 to deflect from 0 degree up to 270 degrees when fully defected. A force sensor, a contact sensor, or other sensing mechanism 518 can be included in the path of the wire 512 or as a part of the wire 512 to detect how much force is applied to the ablation tip 502 while activating or deflecting the distal ablation tip 502 against the tissue TI as shown in FIG. 12. Alternatively or in combination, the contact sensor or force sensor 518 can be included as a part of the distal ablation tip 502 as further described below and herein. For example, the ablation tip 502 can be formed to have a compliant structure or conformable segment 520 (shown by FIG. 13A) that can be deformed once certain force is exerted between the ablation tip 502 and the surrounding tissue TI in contact with (shown by FIG. 13B). One or more force sensors may be provided on the complaint segment 520. A local sensor (e.g., displacement or rotation) can also be utilized to detect and implement the deformation of the compliant structure 520 as a contact or force sensing mechanism. Also, the ablation tip 502 can remain as a rigid structure, but a compliant structure can be placed just behind or around the rigid tip for the contact or force sensing mechanism. FIGS. 13A and 13B can further illustrate how a contact or force sensing mechanism can be placed and implemented on or around the distal ablation tip.

Figure 14A:
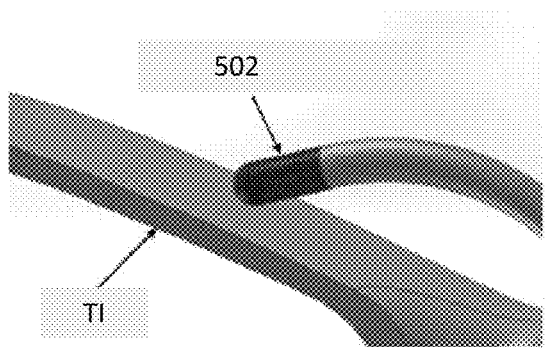
FIG. 14A is a perspective view of a conformable tip of a catheter apparatus that deforms around the tissue, according to many embodiments.
Figure 14B:
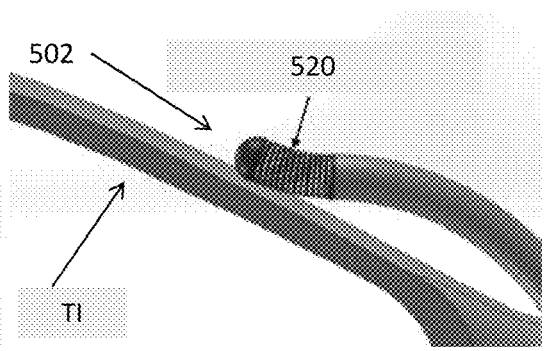
FIG. 14B is a perspective view of the conformable tip of FIG. 14A placed against tissue, according to many embodiments.

The ablation tip 502 and other ablation tips described herein can be a conformable structure, so the tip 502 can conforms around the contact area when placed against the tissue. FIG. 14 shows an example of the conformable tip 502 in a spiral shape that deforms around the surface of the tissue TI when pushed against the tissue TI. The conformable tip shape can be made of various forms and shapes to serve the same purpose. Also, the ablation tip 502 may have enough inner space to accommodate irrigation with fluid (e.g. saline, distilled water, coolant, etc.) to maintain ideal and uniform thermal environment without overheating during ablation.

Figure 15:
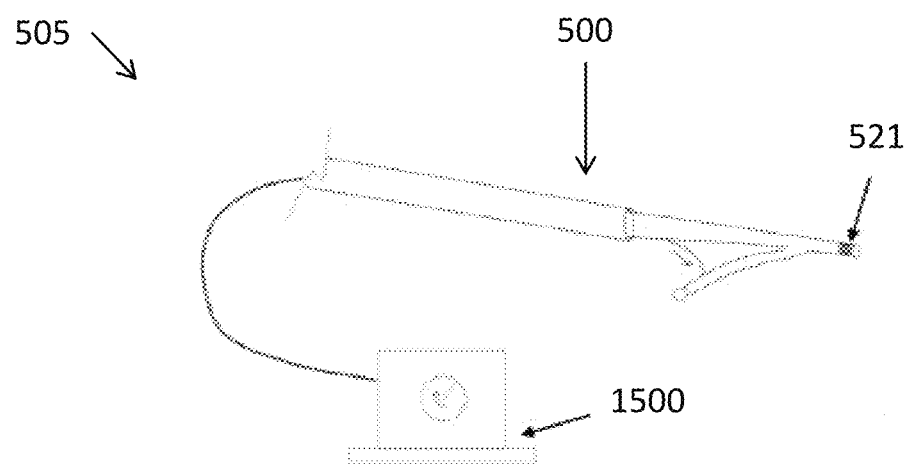
FIG. 15 is a side view of an ablation catheter system with an external display unit connected to an ablation catheter with a local sensor at its distal end to detect and track the orientation of the ablation tip.

Alternatively or in combination, an accelerometer or other local sensor 521 can be placed or embedded at the distal end of the ablation tip 502 and other ablation tips described herein to detect and track the orientation of the ablation tip 502 relative to the pulmonary vein PV (shown by FIG. 15). For complete pulmonary vein isolation, the ablation tip 502 may need to be able to fully rotate 360 degrees and create a complete circular lesion around the pulmonary vein PV. It may be possible to lose the exact orientation of the ablation tip 502 through the lengthy distance of the ablation catheter apparatus 500. When rotating the proximal end, the orientation of the distal end can be lagged behind or may not perfectly match with the orientation of the proximal end. By placing or embedding a local sensor 521 at the distal end, it is possible to detect the exact orientation of the distal ablation tip 502 and track which area has been treated or ablated around the pulmonary vein PV during procedure. There are different types of accelerometers commercially available. Bosch Sensortec's BMC150 (Bosch Sensortec of Reutlingen, Germany) can be a good example to use for the ablation catheter apparatus 500. The BMC150 may comprise a 3-axis geomagnetic sensor and a 3-axis 12 bit accelerometer that come in a small package (2.2 mm×2.2 mm×0.95 mm). The accelerometer may require four small electrical wires for inter-connection, so an external display unit 1500 can be connected through a connector in the proximal end as shown in FIG. 15, which shows an ablation catheter system 550 comprising the ablation catheter apparatus 500 and the external display unit 1500. Alternatively or in combination, the ablation catheter apparatus 500 can be used or integrated with existing mapping systems (e.g. the Ensite NaVx systems available from St. Jude Medical, Inc. of St. Paul, Minn., the CARTO systems available from Biosense Webster, Inc. of Diamond Bar, Calif., etc.). It may be feasible to use existing mapping systems to detect and track the orientation of the ablation tip 502 regardless of the local sensor at the distal end. Also, the local rotational sensor 521 can be combined with externally applied fields to provide three dimensional localization of the ablation tip. For example, the sensor 521 may comprise one or more strain sensitive mechanical films which may have magnetic properties which change as an external force is applied. Magnetic sensing mechanisms are described in U.S. Pub. No. 2011/0184406 to Selkee. Alternatively or in combination, the sensor 521 may comprise reflective surfaces which may have reflective properties which change as an external force is applied. Optical fiber(s) may transmit and receive light within the ablation catheter apparatus 500 and orientation and deflection of the ablation 502 may be determined based on the intensity of the reflected light from the sensor 521. Optical sensing mechanisms are described in U.S. Pat. No. 8,048,063 to Aeby et al. Alternatively or in combination, the ablation catheter apparatus 500 may comprise one or more radiopaque markers disposed at various locations to facilitate imaging of the apparatus 500 during a procedure.

Figure 16A:
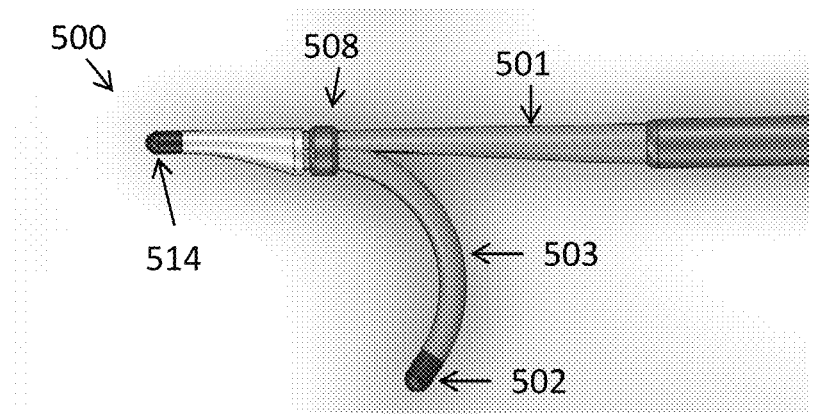
FIG. 16A is a side view of a distal working end of an ablation catheter, according to many embodiments.
Figure 16B:
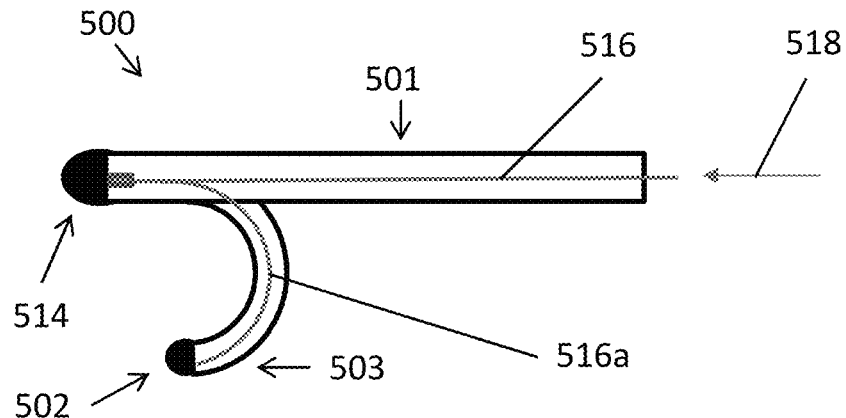
FIG. 16B is a side section view of the ablation catheter working end of FIG. 16A showing its core wire retracted to have the distal working end in a high profile configuration with the laterally extending leg or branch extending laterally outward, according to many embodiments.
Figure 16C:
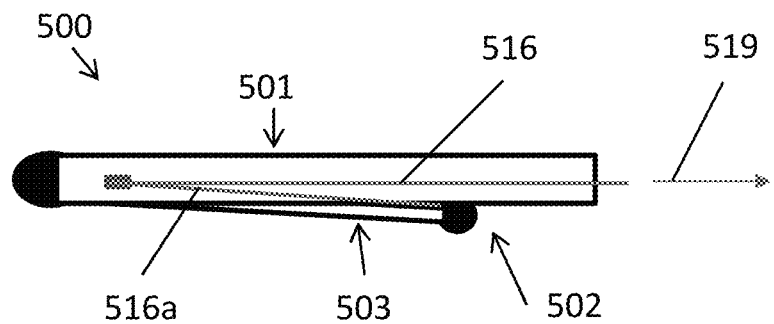
FIG. 16C is a side section view of the ablation catheter working end of FIG. 16A showing its core wire extended to have the distal working end in a low profile configuration with the laterally extending leg or branch retracted toward the longitudinal axis of the ablation catheter, according to many embodiments.
Figure 16D:
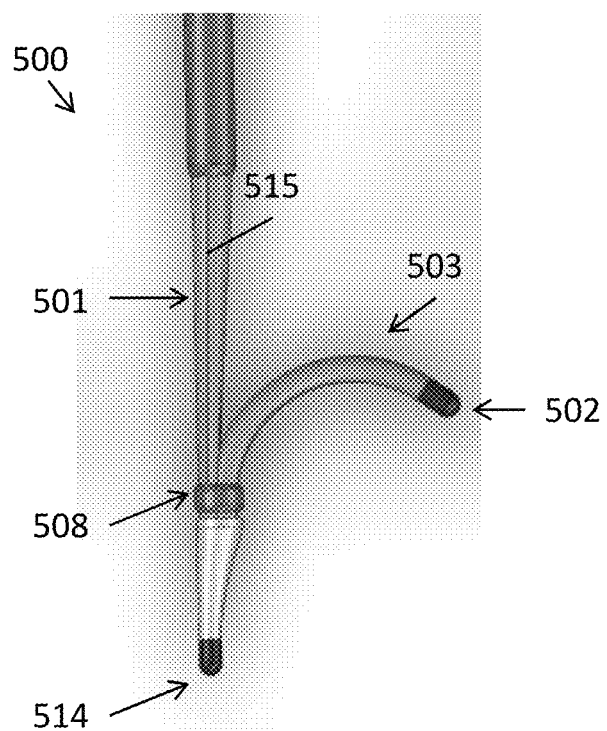
FIG. 16D is a side view of the ablation catheter working end of FIG. 16A showing its constraint extended to have the distal working end in the high profile configuration.
Figure 16E:
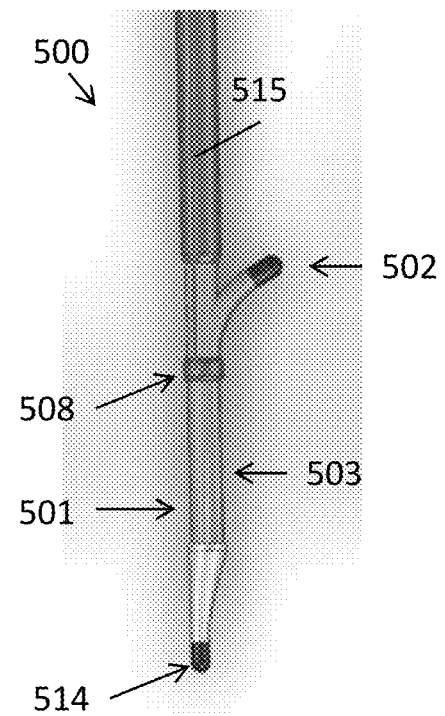
FIG. 16E is a side view of the ablation catheter working end of FIG. 16A showing its constraint retracted to have the distal working end in the low profile configuration.

Referring to FIGS. 16A-16E, the ablation catheter apparatus 500 can be actuated between a high profile configuration with its laterally extending leg or branch 503 branching or extending laterally outward (shown in FIGS. 16B and 16D) and a low profile configuration with its laterally extending leg 503 held substantially parallel to its leg 501 parallel with the elongate main body of the ablation catheter apparatus 500 (shown in FIGS. 16C and 16E). FIG. 16A is a side view of the working end of the ablation catheter apparatus 500 in the high profile configuration where the laterally extending leg 503 extends away from the longitudinal axis of the ablation catheter apparatus 500 and/or the leg 501 in a curved, reverse manner (i.e., so that the ablation tip 502 at its proximal end extend outward and toward the distal end of the ablation catheter apparatus 500.) As shown in FIGS. 16A-16E, the distal most tip of the ablation catheter apparatus 500 may comprise a further effector or ablation tip 514 which may comprise an ablation electrode or other ablation element. Also as shown in FIGS. 16A, 16D, and 16E, the translatable constraint 508 can be in the form of an annular ring circumscribing the legs 501 and 503.

As shown in FIGS. 16A and 16B, the ablation catheter apparatus 500 may further comprise a core wire 516 which may be translated to actuate the ablation catheter apparatus between the high and low profile configurations. The core wire 516 may be disposed within the elongate main body of the ablation catheter apparatus 500 and the leg 501. The core wire 516 may comprise a distal arm or branch 516a branching or extending from the core and disposed within the leg 503. The core wire 516 may be biased to be in a linear configuration (i.e., a straight line) and may be biased to extend laterally outwardly from the core wire 516 in a curved, reverse manner. In doing so, the core wire arm 516a may at least in part provide the curved, reverse shape of the laterally extending leg 503. As shown in FIG. 16B, the core wire 516 may be advanced distally in the direction indicated by arrow 518 so that the constraint 508 or other constraining element may constrain more of the leg 503 such that the leg 503 is pulled toward the leg 501 to assume the configuration shown in FIG. 16C. As shown in FIG. 16C, the core wire 516 may be retracted proximally in the direction indicated by arrow 519 so that the constraint 508 or other constraining element may constrain less of the leg 503 such that the leg 503 can extend laterally outward to assume the configuration shown in FIG. 16B. Alternatively, the core wire 516 may be pulled proximally to extend laterally the leg 503 to assume the configuration shown in FIG. 16B. In a similar fashion, the core wire 516 may be pushed distally to retract the leg 503 toward the leg 501 to assume the configuration shown in FIG. 16C.

Alternatively or in combination, the constraint or movable ring 508 may be retracted from the position shown in FIG. 16D to the position shown in FIG. 16E to move the ablation catheter apparatus 500 between the high and low profile configurations, respectively. The ablation catheter apparatus 500 may comprise a push-pull wire 515 coupled at its distal end to the constraint 508 to translate the constraint 508. The push-pull wire 515 may be disposed within a lumen of the ablation catheter apparatus 500 and the leg 501. The push-pull wire 515 may be proximally retracted to proximally retract the constraint 508 to place the ablation catheter apparatus 500 in the low profile configuration. The push-pull wire 515 may be advanced distally to distally advance the constraint 508 to place the ablation catheter apparatus in the high profile configuration. The push-pull wire 515 may further comprise a proximal end which may be manipulated by the user to translate the push-pull wire 515. For example, the proximal end of the push-pull wire 515 may be coupled to a proximal handle of the ablation catheter apparatus 500.

Figure 17A:
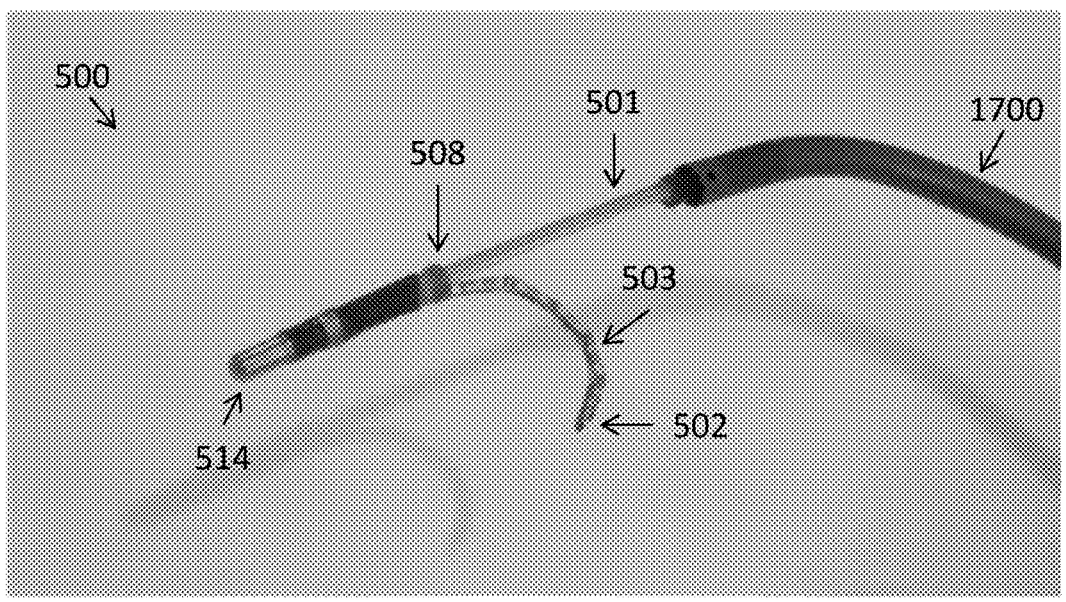
FIGS. 17A, 17B, and 17C are perspective views of an ablation catheter apparatus extending from an introducer sheath, according to many embodiments.
Figure 17B:
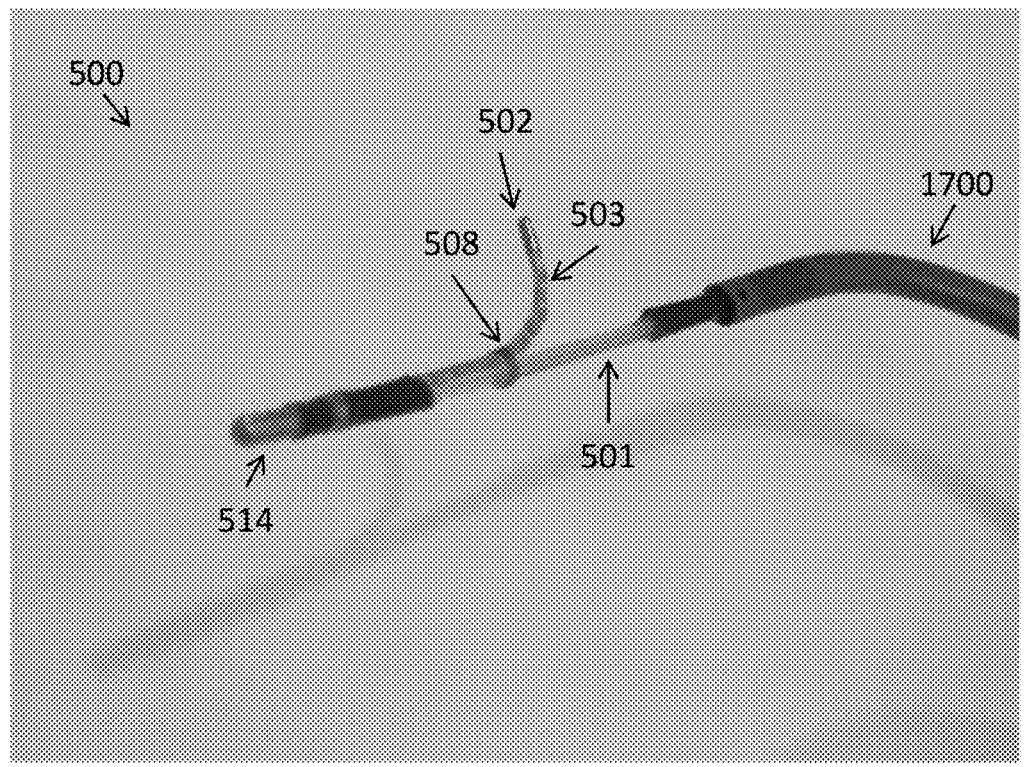
Figure 17C:
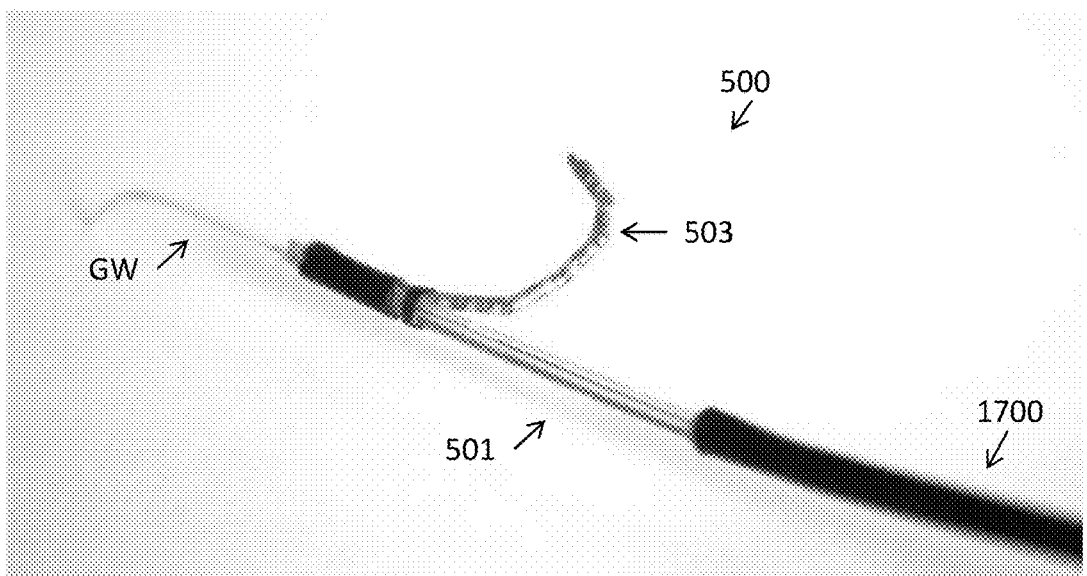

FIGS. 17A, 17B, and 17C are perspective views of the ablation catheter apparatus 500 extending from an introducer sheath 1700. As shown in FIG. 17B, the constraint or annular ring 508 may be proximally retracted to lessen the degree of lateral extension of the lateral leg 503. The ablation catheter apparatus 500 may also be independently rotated relative to the introducer sheath 1700.

The ablation tips 502 and/or 514 can be used in unipolar or bipolar mode. For example, the ablation catheter apparatus 500 may include both ablation tips or electrodes 502, 514 to allow bipolar ablation. The distal ablation tip or electrode 514 may also be used as a mapping tool to measure electrical activity within an anatomical structure such as the pulmonary vein PV. The distal tip of the ablation catheter apparatus 500 can be formed in various shapes (i.e., circular, basket, ring, straight, etc.) The distal tip of the ablation catheter apparatus 500 can have a lumen to deliver or place another separate mapping device. As shown in FIG. 17C, a guidewire GW may be passed through the lumen of the ablation catheter apparatus 500.

Figure 18A:
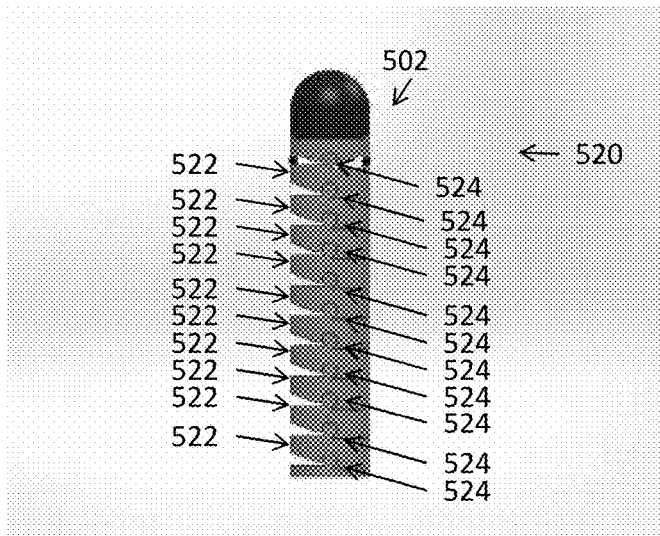
FIGS. 18A and 18B show magnified views of an ablation catheter apparatus ablation tip with a compliant section, according to many embodiments.
Figure 18B:
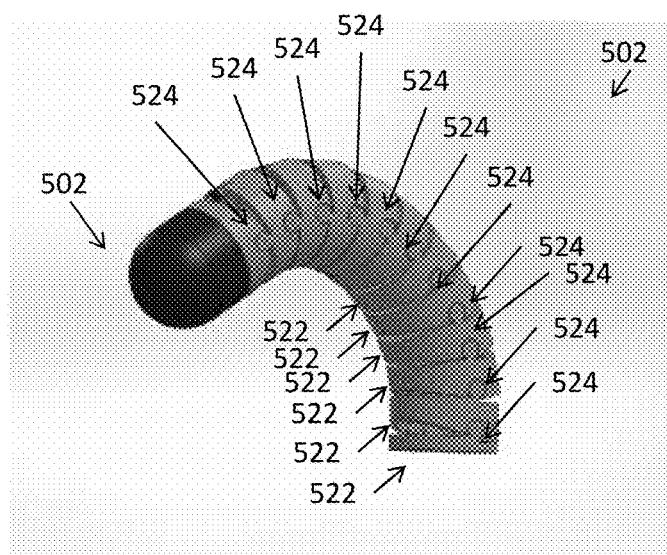

FIGS. 18A and 18B show magnified views of the ablation tip 502 and the compliant section 520. FIG. 18A shows the compliant section 520 in a linear configuration and FIG. 18B shows the compliant section 520 deflected. The compliant section 520 may comprise multiple annular elements 522 joined by rotational joints 524. The annular elements 522 may be slotted or tapered to allow the compliant section 520 to be deflectable around the axis of the rotational joints 524 with minimal off-axis deflection. To generate the annular elements 522 and the rotational joints 524, a single tubular structure such as a metal tube may be processed by a machining or cutting process (e.g., CNC machining, laser-cutting, lithography, etc.), and the annular elements and the rotational joint are created as if they are pre-assembled while it is processed. The rotational joints 524 may be tapered inwardly to prevent lateral forces from displacing the annular elements 522 from one another.

Figure 19A:
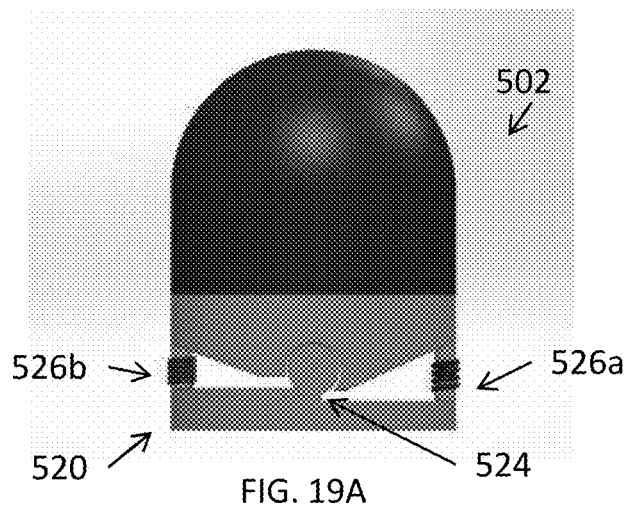
FIG. 19A shows a side view of an ablation catheter apparatus ablation tip or effector with an electro-mechanical contact sensor, according to many embodiments.
Figure 19B:
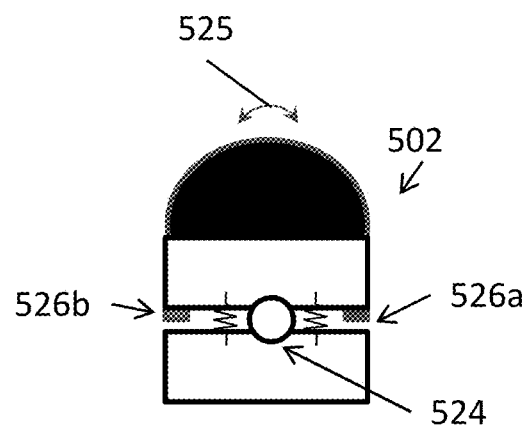
FIG. 19B shows a schematic of the ablation catheter apparatus ablation tip of FIG. 19A.

The ablation catheter 500, particularly the working end, may further comprise a contact sensor or a contact sensing mechanism. As shown in FIGS. 19A and 19B, the contact sensing mechanism may comprise one or more electro-mechanical switches 526a, 526b which may be coupled to the compliant section 520. The contact sensor can be activated with a preset force range (e.g., 5-10 grams, 10-15 grams, 15-20 grams, etc.) Once the contact force(s) or pressure with the tissue reaches this preset force range, the ablation tip 502 may tip, move, or deflect (e.g., in the directions shown by double-sided arrow 525 in FIG. 19B) to activate the electro-mechanical switches 526a and/or 526b. The electro-mechanical switches 526a, 526b may comprise spring-like elements with a preset force range for activation. In a binary mode, tipping the ablation tip 502 may activate one of the electro-mechanical switches 526a, 526b while leaving the other deactivated, thereby indicating the direction of tipping and that the threshold force range has been met.

Figure 20A:
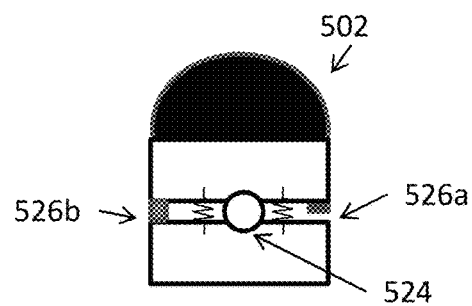
FIGS. 20A, 20B, and 20C show schematics of an ablation catheter apparatus ablation tip or effector configured to sense contact forces in a trinary mode, according to many embodiments.
Figure 20B:
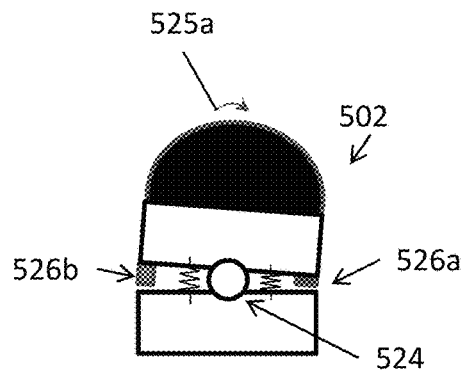
Figure 20C:
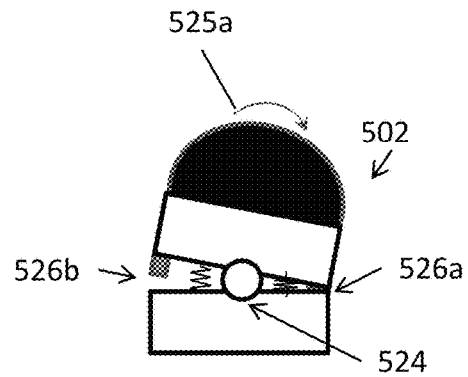

Referring to FIGS. 20A, 20B, and 20C, the electro-mechanical sensing mechanism may also be configured to work in a trinary mode with a single rotation joint 524. As shown in FIG. 20A, with no contact between the tissue and the ablation tip 502, the first electro-mechanical switch 526a may be in an open circuit configuration while the second electro-mechanical switch 526b may be in a closed circuit configuration, which may indicate to a user that there is no contact between the tissue and the ablation tip 502. As shown in FIG. 20B, the ablation tip 502 may be tipped in a direction indicated by the arrow 525a with a sufficient amount of contact between the tissue and the ablation tip 502. Both the first and second electro-mechanical switches 526a, 526b may be in an open circuit configuration to indicate the sufficient amount of contact to the user. As shown in FIG. 20C, the ablation tip 502 may be tipped further in the direction indicated by the arrow 525a with too much contact between the tissue and the ablation tip 502. The excessive contact may cause the first electro-mechanical switch 526a to be in a closed circuit configuration and the second electro-mechanical switch 526b to be in an open circuit configuration, which may indicate to the user that there is excessive contact.

Figure 21A:
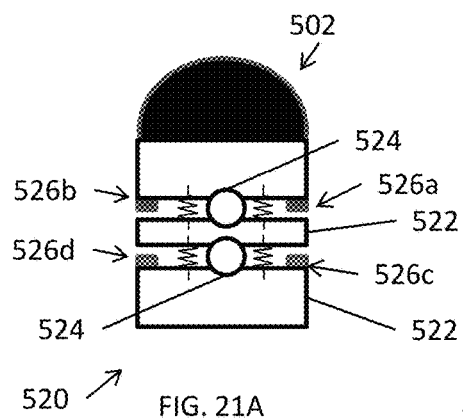
FIGS. 21A, 21B, and 21C show schematics of an ablation catheter apparatus ablation tip or effector configured to sense contact forces with a plurality of electro-mechanical switches disposed on its compliant section, according to many embodiments.
Figure 21B:
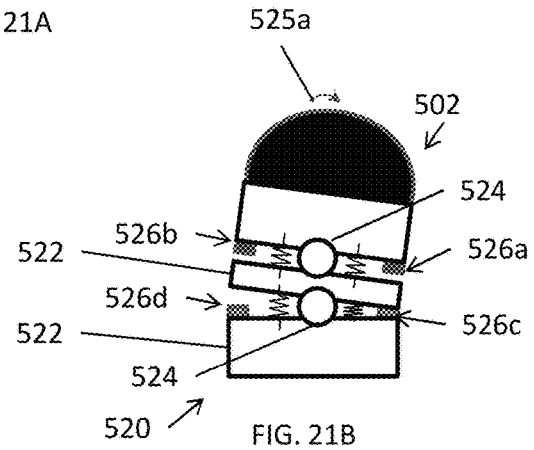
Figure 21C:
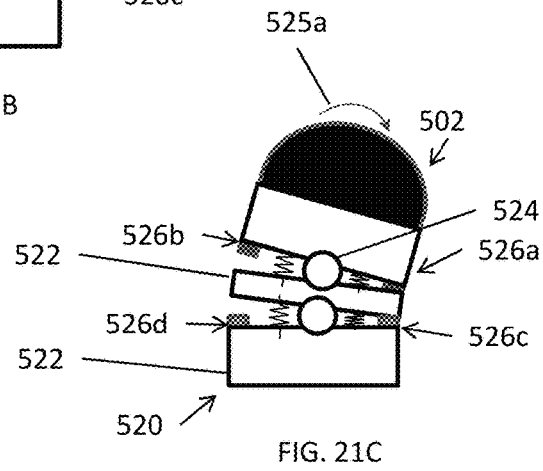

Referring to FIGS. 21A, 21B, and 21C, the ablation catheter apparatus ablation tip 500 may be configured to sense contact forces with a plurality of electro-mechanical switches 526a, 526b, 526c, and 526d disposed between adjacent annular elements 522 in the compliant section 520. As shown by FIG. 21A, the electro-mechanical switches 526a, 526b, 526c, and 526d are in open circuit configurations to indicate no contact between the tissue and the ablation tip 502. As shown by FIG. 22B, the electro-mechanical switches 526a, 526b, and 526d are in open circuit configurations while the electro-mechanical switch 526c is in a closed circuit configuration to indicate sufficient contact between the tissue and the ablation tip 502 as the ablation tip 502 is deflected or tipped in the direction indicated by the arrow 525a. As shown by FIG. 22C, the electro-mechanical switches 526b and 526d are in open circuit configurations while the electro-mechanical switches 526a and 526c are in closed circuit configurations to indicate excessive contact between the tissue and the ablation tip 502 as the ablation tip 502 is deflected or tipped excessively in the direction indicated by the arrow 525a.

Figure 22:
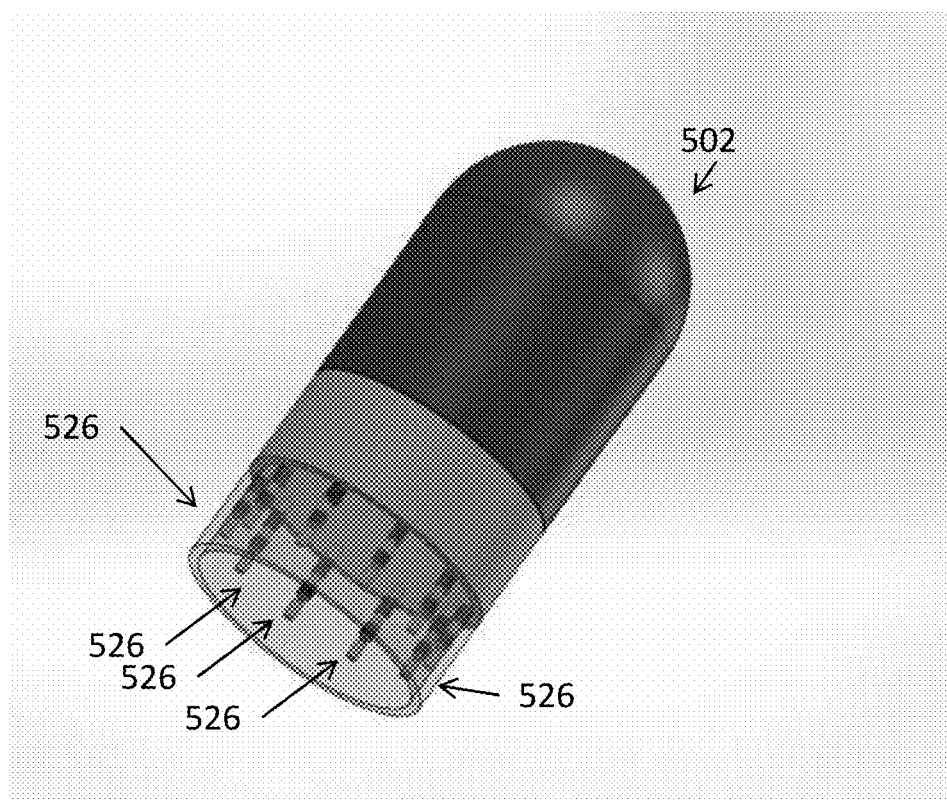
FIG. 22 shows a perspective view of an ablation catheter apparatus ablation tip or effector with a plurality of electro-mechanical switches disposed circumferentially around the ablation tip, according to many embodiments.

Referring to FIGS. 19A to 21C, electro-mechanical switches 526a, 526b (and 526c, 526d) are shown as disposed diametrically on opposite sides of the ablation tip 502 and/or the compliant section 522. Alternatively or in combination, more than two electro-mechanical switches 526 may be provided adjacent the perimeter of the ablation tip 502. As shown in FIG. 22, a plurality of electro-mechanical switches 526 may be provided circumferentially around and proximal the ablation tip 502. By providing more than two contact sensing switches 526, the degree of contact between the ablation tip 502 and the tissue can be determined in more than one-dimension.

Contact and the degree of contact between the ablation tip 502 and the tissue may be indicated by the external display unit which may be coupled to the electro-mechanical switches 526, 526a, 526b, 526c, and/or 526d. Alternatively or in combination, the contact and the degree of contact may be indicated by sound, vibration or light (s) in the proximal handle of the ablation catheter apparatus 500.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. An ablation catheter comprising:
    an elongate catheter body having a central axis, a distal end, and a proximal end, said elongate catheter body configured to be steered within a heart chamber; and
    a branch electrode element having a base end and a working end, wherein the base end is secured to the elongate catheter body at a location spaced proximally of the distal end and an effector on the working end,
    wherein the branch electrode element is configured to evert when the distal end of the elongate catheter body is in a pulmonary vein os so that the effector can be selectively engaged against locations surrounding the pulmonary vein os which differ in radial direction and distance,
    wherein the branch electrode element is curved when everted, and
    wherein the branch electrode is curved to match a curvature of a pulmonary vein or the pulmonary vein os.

2. The ablation catheter of claim 1, further comprising a constraint coupled to the branch electrode element to adjust an amount of eversion of the branch electrode element.

3. The ablation catheter of claim 2, wherein the constraint is configured to be translated relative to one or more of the elongate catheter body or the branch electrode element to adjust the amount of eversion of the branch electrode element.

4. The ablation catheter of claim 2, wherein the constraint is annular and circumscribes one or more of the elongate catheter body or the branch electrode element.

5. The ablation catheter of claim 2, further comprising a push-pull wire coupled to the elongate catheter body and the constraint, wherein the push-pull wire is configured to be translated to adjust the amount of eversion of the branch electrode element.

6. The ablation catheter of claim 5, wherein the push-pull wire is configured to be proximally retracted to reduce the amount of eversion of the branch electrode element.

7. The ablation catheter of claim 1, further comprising a core wire disposed within the elongate catheter body, the core wire having a coaxial distal portion disposed within the elongate catheter body and a lateral arm coupled to the straight coaxial distal portion and disposed within the branch electrode element.

8. The ablation catheter of claim 7, wherein proximal retraction of the core wire causes the lateral arm to extend laterally outward, everting the branch electrode element.

9. The ablation catheter of claim 7, wherein distal advancement of the core wire straightens the lateral arm, reducing eversion of the branch electrode element.

10. The ablation catheter of claim 1, further comprising a distal anchor extending from the distal end of the elongate catheter body, the distal anchor configured to be seated within a lumen of the pulmonary vein.

11. The ablation catheter of claim 10, wherein the distal anchor is coaxial with the central axis of the elongate catheter body.

12. The ablation catheter of claim 10, wherein the branch electrode element is rotatable with respect to the distal anchor.

13. The ablation catheter of claim 10, wherein the distal anchor comprises one or more mapping electrodes.

14. The ablation catheter of claim 1, wherein the effector comprises an ablation electrode.

15. The ablation catheter of claim 1, wherein the branch electrode element comprises a sensor to detect one or more of contact force or pressure with tissue, an orientation of effector, or a position of the effector.

16. The ablation catheter of claim 15, wherein the sensor comprises one or more of an accelerometer, a strain gauge, an optical indicator, a magnetic position indicator, or a piezoelectric element.

17. The ablation catheter of claim 1, wherein the branch electrode element comprises a deflectable or compliant section.

18. The ablation catheter of claim 17, wherein the deflectable or compliant section comprises one or more rotational joints and annular segments.

19. A method for pulmonary vein ablation, said method comprising:
anchoring a distal end of a catheter in a pulmonary vein os; and
deploying a branch electrode element which carries an ablation element to a plurality of locations surrounding the pulmonary vein,
wherein deploying includes independently controlling the radial direction and radial distance of the ablation element from the catheter.

20. The method of claim 19, wherein anchoring the distal end of the catheter in the pulmonary vein os comprises expanding an expandable element in the pulmonary vein.

21. The method of claim 20, wherein the expandable element comprises a wire cage or an inflatable balloon.

22. The method of claim 19, further comprising mapping tissue surrounding the pulmonary vein os with one or more mapping electrodes disposed on the distal end of the catheter.

23. The method of claim 19, further comprising generating an ablation pattern on tissue adjacent the pulmonary vein os with the ablation element.

24. The method of claim 23, wherein generating the ablation pattern comprises rotating the catheter to generate a curved ablation pattern with the ablation element.

25. The method of claim 23, wherein generating the ablation pattern comprises axially translating the catheter to generate a linear ablation pattern with the ablation element.

26. The method of claim 23, wherein generating the ablation pattern comprises adjusting an amount of eversion of the branch electrode element relative to the catheter.

27. The method of claim 23, wherein generating the ablation pattern comprises delivering energy from the ablation element to the tissue.

28. The method of claim 27, wherein the energy delivered comprises one or more of RF energy or thermal energy.

29. The method of claim 27, wherein the ablation element comprises an ablation electrode.

30. The method of claim 23, wherein generating the ablation pattern comprises delivering a cooling fluid for cryoablation.

31. The method of claim 19, further comprising determining a tissue contact force between the ablation element and tissue surrounding the pulmonary os.

32. The method of claim 31, wherein the tissue contact force is determined with a sensor adjacent the ablation element.

33. The method of claim 19, further comprising determining one or more of an orientation or position of the ablation element.

34. The method of claim 33, wherein the orientation or position of the ablation element is determined with a sensor adjacent the ablation element.

35. A method for tissue ablation, said method comprising:
anchoring a distal end of a catheter in an opening into a body cavity; and
deploying a branch electrode element which carries an ablation element to a plurality of tissue locations surrounding the opening into the body cavity,
wherein deploying includes independently controlling the radial direction and radial distance of the ablation element from the catheter.

36. The method of claim 35, wherein the body cavity is selected from the group comprising a nasal cavity, an oral cavity, a throat, an esophagus, a stomach, a small intestine, a large intestine, a colon, a rectum, a bronchus, a bladder, a ureter, a urethra, a vagina, a cervix, a uterus, a fallopian tube, a heart chamber, a heart ventricle, a heart atrium, an aorta, a vena cava, an abdominal aorta, a renal artery, a femoral artery, an ascending aorta, a subclavian artery, a carotid artery, a jugular vein, a subclavian vein, a cephalic vein, a femoral vein, a renal vein, an inferior vena cava, or a pulmonary artery.

* * * * *